US011667721B2

(12) United States Patent
Medin et al.

(10) Patent No.: US 11,667,721 B2
(45) Date of Patent: *Jun. 6, 2023

(54) CD30 BISPECIFIC ANTIBODIES AND METHOD OF IMMUNOTHERAPY OF CD30+ MALIGNANCIES

(71) Applicants: MEDICAL COLLEGE OF WISCONSIN, INC., Milwaukee, WI (US); UNIVERSITY OF VIRGINIA PATENT FOUNDATION, Charlottesville, VA (US)

(72) Inventors: Jeffrey A. Medin, Shorewood, WI (US); Lawrence G. Lum, Charlottesville, VA (US); Robyn A. A. Oldham, Milwaukee, WI (US); Archana Thakur, Charlottesville, VA (US)

(73) Assignees: Medical College of Wisconsin, Inc., Milwaukee, WI (US); University of Virginia Patent Foundation, Charlottesville, VA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/580,625

(22) Filed: Sep. 24, 2019

(65) Prior Publication Data

US 2020/0095330 A1    Mar. 26, 2020

Related U.S. Application Data

(60) Provisional application No. 62/735,576, filed on Sep. 24, 2018.

(51) Int. Cl.
*C07K 16/28* (2006.01)
*A61K 39/395* (2006.01)
*A61P 35/00* (2006.01)

(52) U.S. Cl.
CPC .... *C07K 16/2878* (2013.01); *A61K 39/39583* (2013.01); *A61P 35/00* (2018.01); *C07K 16/283* (2013.01); *C07K 16/2809* (2013.01); *A61K 39/3955* (2013.01); *C07K 2317/31* (2013.01); *C07K 2317/565* (2013.01); *C07K 2317/732* (2013.01)

(58) Field of Classification Search
CPC ............ C07K 16/2878; C07K 16/2809; C07K 16/283; C07K 2317/31
See application file for complete search history.

(56) References Cited

U.S. PATENT DOCUMENTS 5,731,168 A    3/1998 Carter et al.

FOREIGN PATENT DOCUMENTS

| EP | 1870459 | 6/2016 |
|---|---|---|
| WO | 2003059282 | 7/2003 |
| WO | 2007110205 | 10/2007 |
| WO | 2008119353 | 10/2008 |
| WO | 2009089004 | 7/2009 |
| WO | 2011131746 | 10/2011 |
| WO | 2017066122 | 4/2017 |
| WO | 2018158350 | 9/2018 |

OTHER PUBLICATIONS

Da Costa et al (2000. Cancer Chemother Pharmacol. 46(Suppl): S33-S36).*
Renner et al, 1995. Immunological Reviews. 145: 179-209.*
Ferrara et al (2015. mAbs. 7(1): 32-41).*
Kuhn et al, 2016. Immunology. 8(8): 889-906.*
Gillis, 2017. J Allergy Clin Immunol. 139:1253-65.*
Grudzien et al, 2018. J Immunol Res. pp. 1-11.*
Bargou, et al. Tumor regression in cancer patients by very low doses of a T cell-engaging antibody. Science. 2008; 321(5891), 974-977.
Bird et al. Single-chain antigen-binding proteins. Science 1988; 242: 423-426.
Carde P, Da Costa L, Manil L, et al. Immunoscintigraphy of Hodgkin's disease: in vivo use of radiolabelled monoclonal antibodies derived from Hodgkin cell lines. Eur J Cancer. 1990;26(4):474-479. doi:10.1016/0277-5379(90)90019-p.
Chiarle R, Podda A, Prolla G, Gong J, Thorbecke GJ, Inghirami G. CD30 in normal and neoplastic cells. Clin Immunol. 1999;90: 157-164.
Elgundi, et al. The state-of-play and future of antibody therapeutics. Advanced Drug Delivery Reviews 2017. 122: 2-19.
Froese et al., Biochemical characterization and biosynthesis of the Ki-1 antigen in Hodgkin-derived and virus-transformed human B and T lymphoid cell lines. J Immunol Sep. 15, 1987, 139 (6) 2081-2087.
Huston et al. Protein engineering of antibody binding sites: recovery of specific activity in an anti-digoxin single-chain Fv analogue produced in *Escherichia coli*. PNAS USA 1988; 85: 5879-5883.
Lindhofer et al. Preferential species-restricted heavy/light chain pairing in rat/mouse quadromas. Implications for a single-step purification of bispecific antibodies. J Immunol 1995; 155(1): 219-225.
Lum, et al. CD20-Targeted T Cells after Stem Cell Transplantation for High Risk and Refractory Non-Hodgkin's Lymphoma. Biology of Blood and Marrow Transplantation 2013; 19(6): 925-933.
Lum, et al. Targeting T Cells with Bispecific Antibodies for Cancer Therapy. BioDrugs 2011; 25(6): 365-379.
Marvin, et al. Recombinant approaches to IgG-like bispecific antibodies. Acta Pharmacol Sin. 2005; 26(6): 649-658.
Neut Kolfschoten et al. Anti-Inflammatory Activity of Human IgG4 Antibodies by Dynamic Fab Arm Exchange Science. 2007; 317: 1554-7.
Nitta, et al. Bispecific F (ab') 2 monomer prepared with anti-CD3 and anti-tumor monoclonal antibodies is most potent in induction of cytolysis of human T cells. Eur. J. Immunol. 1989.19: 1437-1441.

(Continued)

*Primary Examiner* — Zachary C Howard
(74) *Attorney, Agent, or Firm* — Quarles & Brady LLP

(57) ABSTRACT

The present invention provides novel bispecific antibodies that bind to human CD30 and uses thereof. Methods of treating cancer using the bispecific antibodies described herein are also provided.

17 Claims, 15 Drawing Sheets
(13 of 15 Drawing Sheet(s) Filed in Color)
Specification includes a Sequence Listing.

(56) References Cited

OTHER PUBLICATIONS

PCT/US2019/052631—International Search Report and Written Opinion, dated Jan. 20, 2020.
Perez, et al. Specific Targeting of Human Peripheral Blood T Cells by Heteroaggregates Containing Anti-T3 Crosslinked to Anti-Target Cell Antibodies. J. Exp. Med. 1986; 163: 166-178.
Salmeron, et al. A conformational epitope expressed upon association of CD3-epsilon with either CD3-delta or CD3-gamma is the main target for recognition by anti-CD3 monoclonal antibodies. J. Immunol. 1991; 147: 3047-3052.
Schwab, U., Stein, H., Gerdes, J. et al. Production of a monoclonal antibody specific for Hodgkin and Sternberg-Reed cells of Hodgkin's disease and a subset of normal lymphoid cells. Nature 299, 65-67 (1982). https://doi.org/10.1038/299065a0.
Sebastian, et al. Treatment of non-small cell lung cancer patients with the trifunctional monoclonal antibody catumaxomab (anti-EpCAM× anti-CD3): a phase I study. Cancer Immunol Immunotherapy 2007; 56(10): 1637-1644.
Spiess, et al. Alternative molecular formats and therapeutic applications for bispecific antibodies. Molecular Immunology 2015. 67: 95-106.
Thakur, et al. Bispecific antibody based therapeutics: Strengths and challenges. Blood Reviews 2018; 32: 339-347.
Thakur, et al. Cancer therapy with bispecific antibodies: Clinical experience. Curr Opin Mol Ther. 2010; 12(3): 340-349.

\* cited by examiner

Light chain

|      | 3D10 | 10C2 | 12B1 | 15H1 | 15B5 |
|------|------|------|------|------|------|
| 15B5 | 78%  | 52%  | 94%  | 56%  | ---  |
| 15H1 | 59%  | 54%  | 54%  | ---  |      |
| 12B1 | 73%  | 52%  | ---  |      |      |
| 10C2 | 55%  | ---  |      |      |      |
| 3D10 | ---  |      |      |      |      |
| AG10 | 56%  | 60%  | 50%  | 59%  | 50%  |

FIG. 3A

Heavy chain

|      | 3D10 | 10C2 | 12B1 | 15H1 | 15B5 |
|------|------|------|------|------|------|
| 15B5 | 85%  | 68%  | 90%  | 87%  | ---  |
| 15H1 | 90%  | 70%  | 86%  | ---  |      |
| 12B1 | 86%  | 73%  | ---  |      |      |
| 10C2 | 70%  | ---  |      |      |      |
| 3D10 | ---  |      |      |      |      |
| AG10 | 72%  | 70%  | 72%  | 73%  | 70%  |

FIG. 3B mAb binding assays

Cytokine secretion

FIG. 18A
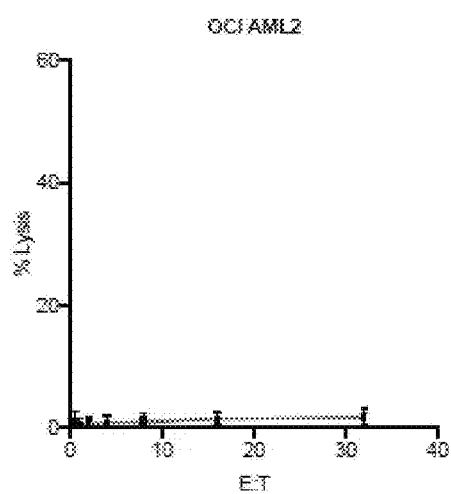
FIG. 18B
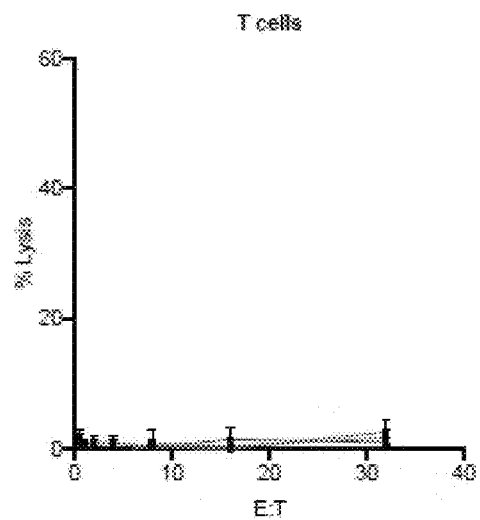
FIG. 19A
| Antibody | $K_A$ (M$^{-1}$) | $k_a$ (Ms$^{-1}$) | $K_D$ (nM) | $k_d$ (s$^{-1}$) |
|---|---|---|---|---|
| 8D10 | 16.9 x 10$^9$ | 10.1 x 10$^4$ | 0.0592 | 0.6 x 10$^{-5}$ |
| 10C2 | 1.65 x 10$^9$ | 30.7 x 10$^4$ | 0.607 | 18.6 x 10$^{-5}$ |
| 12B1 | 5.02 x 10$^9$ | 6.13 x 10$^4$ | 0.199 | 1.22 x 10$^{-5}$ |
| 13H1 | 6.7 x 10$^9$ | 70.8 x 10$^4$ | 0.149 | 10.6 x 10$^{-5}$ |
| 15B8 | 1.02 x 10$^9$ | 50.4 x 10$^4$ | 0.978 | 49.3 x 10$^{-5}$ |
FIG. 19B
| Antibody | $K_A$ (M$^{-1}$) | $k_a$ (Ms$^{-1}$) | $K_D$ (nM) | $k_d$ (s$^{-1}$) |
|---|---|---|---|---|
| 8D10 | 8.78 x 10$^5$ | 4.53 x 10$^3$ | 1.14 | 5.23 x 10$^{-3}$ |
| 10C2 | 5.79 x 10$^5$ | 5.88 x 10$^3$ | 1.76 | 10.1 x 10$^{-3}$ |
| AC10 | 9.03 x 10$^7$ | 1.82 x 10$^5$ | 11.1nM | 2.02 x 10$^{-3}$ |

US 11,667,721 B2

CD30 BISPECIFIC ANTIBODIES AND METHOD OF IMMUNOTHERAPY OF CD30+ MALIGNANCIES

CROSS-REFERENCE TO RELATED APPLICATIONS

This application claims priority to U.S. Application No. 62/735,576 filed on Sep. 24, 2018, the contents of which is incorporated by reference in its entirety.

STATEMENT REGARDING FEDERALLY SPONSORED RESEARCH

N/A

BACKGROUND OF THE INVENTION

The field of the invention is novel bispecific antibodies specific to human CD30, and the use thereof.

Bispecific antibodies (BiAb) include antibodies or antibody-like molecules that contain two different binding specificities by combining two different binding moieties. BiAbs have been studied to be used as immunotherapy for tumors in order to increase the immune response against tumor antigens and thus tumor cells.

CD30 cell surface molecule is a member of the tumor necrosis factor receptor (TNF-R) superfamily and a transmembrane glycoprotein preferentially expressed by activated lymphoid cells. This family of molecules has variable homology among its members and includes nerve growth factor receptor (NGFR), CD120(a), CD120(b), CD27, CD40 and CD95. Members of this family play a role in regulating proliferation and differentiation of lymphocytes.

CD30 was originally identified by the monoclonal antibody Ki-1, which is reactive with antigens expressed on Hodgkin and Reed-Sternberg cells of Hodgkin's disease (Schwab et al., *Nature* 299:65 (1982)). CD30 has been used as a clinical marker for Hodgkin's lymphoma and related hematological malignancies (Froese et al., *J. Immunol.* 139: 2081 (1987); Carde et al., *Eur. J. Cancer* 26:474 (1990)). It has since been found on a number of hematologic malignancies. Since the percentage of CD30-positive cells in normal individuals is very low, CD30 in tumor cells renders it an important target for antibody mediated therapy to specifically target therapeutic agents against CD30-positive neoplastic cells (Chaiarle, R., et al. *Clin. Immunol.* 90(2): 157-164 (1999)).

Hodgkin Lymphoma (HL) is often treatable, with 86% surviving over 5 years. However, about 30% of patients relapse, a subset of which develop resistant HL. Refractory or relapsed chemo-resistant disease is more challenging to treat: the 5-year survival rate for these patients is just 31%. CD30 is also expressed in a substantial subset of patients with acute myeloid leukemia (AML) which accounts for 1.2% of all cancer cases in the United States and has a 5-year survival rate of just 26.6%. Relapse following initial therapy is common, and patients who relapse after a stem cell transplantation are typically non-responsive to further therapeutic intervention.

Accordingly, the need exists for improved bispecific antibodies that can target CD30+ cancers.

SUMMARY OF THE INVENTION

The present invention addresses the aforementioned drawbacks by providing isolated bispecific antibodies able to bind CD30 antibodies and a T-cell or NK cell surface antigen for example CD-3. A particular embodiment is a bispecific antibody comprising an anti-CD30 and an anti-CD3 antibody or antigen binding fragment thereof covalently linked. The bispecific antibodies described herein can be used for methods of treating patient populations having CD30+ cancers.

In one aspect, the present disclosure provides an isolated bispecific antibody capable of binding human CD30 and to a T cell surface antigen comprising a CD30 antibody or antigen binding portion thereof and a T cell surface antigen antibody or antigen binding portion thereof, In another aspect, the present disclosure provides an isolated bispecific antibody capable of binding human CD30 and to a T cell surface antigen comprising a CD30 antibody or antigen binding portion thereof and a T cell surface antigen antibody or antigen binding portion thereof, the CD30 antibody or antigen binding portion thereof comprising (a) a light chain variable domain comprising a CDRL1 region of SEQ ID NO:2 or a sequence with 85% similarity to SEQ ID NO:2, a CDRL2 region of SEQ ID NO:3 or a sequence with 85% similarity to SEQ ID NO:3, and a CDRL3 region of SEQ ID NO:4 or a sequence with 85% similarity to SEQ ID NO:4 and a heavy chain variable domain comprising a CDRH1 region of SEQ ID NO:6 or a sequence with 85% similarity to SEQ ID NO:6, a CDRH2 region of SEQ ID NO:7 or a sequence with 85% similarity to SEQ ID NO:7, and a CDRH3 region of SEQ ID NO:8 or a sequence with 85% similarity to SEQ ID NO:8;

(b) a light chain variable domain comprising a CDRL1 region of SEQ ID NO: 10 or a sequence with 85% similarity to SEQ ID NO: 10, a CDRL2 region of SEQ ID NO: 11 or a sequence with 85% similarity to SEQ ID NO:11, and a CDRL3 region of SEQ ID NO:12 or a sequence with 85% similarity to SEQ ID NO: 12 and a heavy chain variable domain comprising a CDRH1 region of SEQ ID NO:14 or a sequence with 85% similarity to SEQ ID NO:14a CDRH2 region of SEQ ID NO:15 or a sequence with 85% similarity to SEQ ID NO:15, and a CDRH3 region of SEQ ID NO:16 or a sequence with 85% similarity to SEQ ID NO:16, (c) a light chain variable domain comprising a CDRL1 region of SEQ ID NO:18, a CDRL2 region of SEQ ID NO:19, and a CDRL3 region of SEQ ID NO:20 and a heavy chain variable domain comprising a CDRH1 region of SEQ ID NO:22, a CDRH2 region of SEQ ID NO:23, and a CDRH3 region of SEQ ID NO:24, (d) a light chain variable domain comprising a CDRL1 region of SEQ ID NO:26, a CDRL2 region of SEQ ID NO:27, and a CDRL3 region of SEQ ID NO:28 and a heavy chain variable domain comprising a CDRH1 region of SEQ ID NO:30, a CDRH2 region of SEQ ID NO:31, and a CDRH3 region of SEQ ID NO:32, or (e) a light chain variable domain comprising a CDRL1 region of SEQ ID NO:34, a CDRL2 region of SEQ ID NO:35, and a CDRL3 region of SEQ ID NO:36 and a heavy chain variable domain comprising a CDRH1 region of SEQ ID NO:38, a CDRH2 region of SEQ ID NO:39, and a CDRH3 region of SEQ ID NO:40. In a preferred embodiment, the T cell surface antigen is CD3.

In another aspect, the present invention provides an isolated bispecific antibody capable of binding human CD30 and to a NK cell surface antigen, the bispecific antibody comprising a CD30 antibody or antigen binding portion thereof and a NK cell surface antigen antibody or antigen binding portion thereof, the CD30 antibody or antigen binding portion thereof comprising (a) a light chain variable domain comprising a CDRL1 region of SEQ ID NO:2 or a sequence with 85% similarity to SEQ ID NO:2, a CDRL2 region of SEQ ID NO:3 or a sequence with 85% similarity to SEQ ID NO:3, and a CDRL3 region of SEQ ID NO:4 or a sequence with 85% similarity to SEQ ID NO:4 and a heavy chain variable domain comprising a CDRH1 region of SEQ ID NO:6 or a sequence with 85% similarity to SEQ ID NO:6, a CDRH2 region of SEQ ID NO:7 or a sequence with 85% similarity to SEQ ID NO:7, and a CDRH3 region of SEQ ID NO:8 or a sequence with 85% similarity to SEQ ID NO:8;

(b) a light chain variable domain comprising a CDRL1 region of SEQ ID NO: 10 or a sequence with 85% similarity to SEQ ID NO: 10, a CDRL2 region of SEQ ID NO: 11 or a sequence with 85% similarity to SEQ ID NO: 11, and a CDRL3 region of SEQ ID NO: 12 or a sequence with 85% similarity to SEQ ID NO: 12 and a heavy chain variable domain comprising a CDRH1 region of SEQ ID NO:14 or a sequence with 85% similarity to SEQ ID NO:14a CDRH2 region of SEQ ID NO:15 or a sequence with 85% similarity to SEQ ID NO:15, and a CDRH3 region of SEQ ID NO: 16 or a sequence with 85% similarity to SEQ ID NO: 16, (c) a light chain variable domain comprising a CDRL1 region of SEQ ID NO:18, a CDRL2 region of SEQ ID NO:19, and a CDRL3 region of SEQ ID NO:20 and a heavy chain variable domain comprising a CDRH1 region of SEQ ID NO:22, a CDRH2 region of SEQ ID NO:23, and a CDRH3 region of SEQ ID NO:24, (d) a light chain variable domain comprising a CDRL1 region of SEQ ID NO:26, a CDRL2 region of SEQ ID NO:27, and a CDRL3 region of SEQ ID NO:28 and a heavy chain variable domain comprising a CDRH1 region of SEQ ID NO:30, a CDRH2 region of SEQ ID NO:31, and a CDRH3 region of SEQ ID NO:32, or (e) a light chain variable domain comprising a CDRL1 region of SEQ ID NO:34, a CDRL2 region of SEQ ID NO:35, and a CDRL3 region of SEQ ID NO:36 and a heavy chain variable domain comprising a CDRH1 region of SEQ ID NO:38, a CDRH2 region of SEQ ID NO:39, and a CDRH3 region of SEQ ID NO:40. In a preferred embodiment, the NK cell surface antigen is CD16.

In yet another aspect, the present disclosure provides pharmaceutical compositions comprising the bispecific antibody described herein.

In another aspect, the present disclosure provides a method of treating a patient having a CD30+ cancer, the method comprising (a) administering a therapeutically effective amount of the bispecific antibody described herein to reduce or inhibit CD30+ cancer growth.

In another aspect, the present disclosure provides a method of inhibiting growth of a tumor cell expressing CD30, comprising contacting the tumor cell with an effective amount of the bispecific antibody described herein such that the growth of the cell is inhibited.

The foregoing and other aspects and advantages of the invention will appear from the following description. In the description, reference is made to the accompanying drawings which form a part hereof, and in which there are shown, by way of illustration, preferred embodiments of the invention. Such embodiments do not necessarily represent the full scope of the invention, however, and reference is made therefore to the claims and herein for interpreting the scope of the invention.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 3A depicts the percent identity between the light chains of the novel CD30 antibodies to each other and the known CD30 antibody AC10.

FIG. 3B depicts the percent identity between the heavy chains of the novel CD30 antibodies to each other and the known CD30 antibody AC10.

FIG. 14A shows a representative drawing of the anatomy of one embodiment of bispecific antibodies of the present invention. FIG. 14B shows flow cytometry analysis of biAb binding to CD3+ or CD30+ cells. FIG. 14C demonstrates the conjugation assay design. FIG. 14D shows a summary of results from the conjugation assay. FIG. 14E shows a representative flow cytometry plots from the conjugation assay showing a mixture of biAb-armed T cells and CD30+ tumour analysed by flow. Panel 1 is unarmed T cells, panel 2 is 8D10 biAb-armed T cells, and panel 3 is 10C2 biAb-armed T cells.

FIGS. 18A-18B demonstrate CD30 negative control cell (FIG. 18A) are not killed by biAb-armed T cells and that the CD30 expression on activated T cells is low enough to avoid elimination by the 8D10 and 10C2 biAb armed T cells (FIG. 18B). Experiment was done similar to FIG. 17A-17D.

FIGS. 19A-19B demonstrates surface palsmon resonance (SPR) analysis of CD30 mAbs using two approaches. FIG. 19A shows the results when CD30 protein was immobilized on a CM5 chip, and the antibodies were flowed as an analyte to assess affinity. FIG. 19B shows the results when 8D10, 10C2, or AC10 antibody was immobilized on a Protein G chip, and CD30 protein was flowed as an analyte to assess affinity.

DETAILED DESCRIPTION

Figure 1:
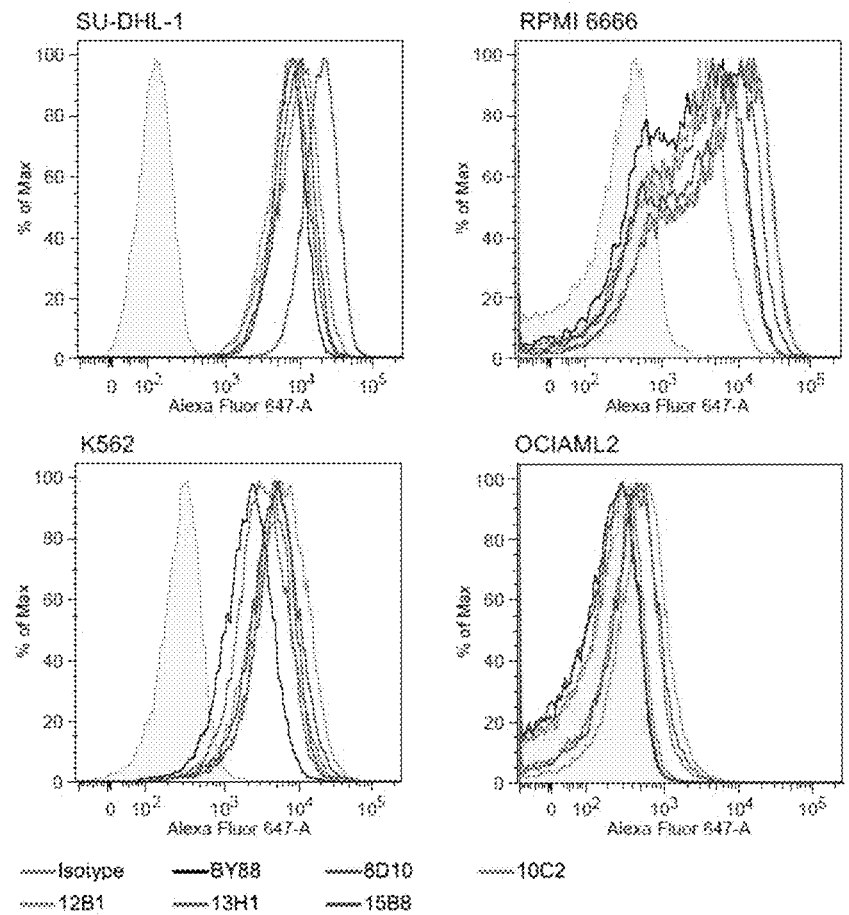
FIG. 1 depict the specific binding of novel CD30 antibody clones to CD30– and CD30+ cells. Flow cytometry analysis was preformed using purified antibody on CD30+ cell lines (SU-DHL-1, RPM16666, 562) and a CD30– cell line (OCIAML2). A commercially available α-huCD30 antibody (clone BY88) and an isotype control were also tested.

The present invention provides isolated bispecific antibodies that can specifically/selectively bind to CD30+ cells and to T cells or NK cells simultaneously. Specifically, in one embodiment, a bispecific antibody that binds to CD30+ and the T cell surface protein CD3 is provided. The present invention also provides in some embodiments methods of treating a subject having a CD30+ tumor using the bispecific antibodies described more herein. In another embodiment, the present disclosure provides a method of inhibiting growth of a tumor cell by administering an effective amount of the bispecific antibodies described herein. In yet another embodiment, the present disclosure provides a method of enhancing a T cell-mediated immune response against a CD30+ tumor cell, the method comprising administering a therapeutically effective amount of the bispecific antibody described herein to increase the T cell-mediated immune response as compared to treatment without the bispecific antibody.

The term "bispecific antibody" as used herein means an antibody, such as a recombinant antibody capable of specifically and selectively recognizing and binding two different antigens. The antibody can be produced by methods known in the art, including chemical linkage or cell fusion methods. In the present disclosure the bispecific antibody is able to bind (a) CD30 and (b) a T cell or NK cell surface antigen. Specifically, in one embodiment, the bispecific antibody is able to bind (a) CD30 and (b) CD3.

In one embodiment, the bispecific antibody comprises (a) a CD30 binding antibody or antigen binding fragment thereof and (b) a T cell surface antigen biding antibody or antigen binding fragment thereof. In one embodiment, both the CD30 and T cell surface antigen binding antibodies or antigen binding fragments are two different antibodies that are covalently or non-covalently linked to each other. In a specific embodiment, the bispecific antibody is a CD30 antibody covalently linked to a CD3 antibody.

The terms "antibody" or "antibody molecule" are used herein interchangeably and refer to immunoglobulin molecules or other molecules which comprise an antigen binding domain. The term "antibody" or "antibody molecule" as used herein is thus intended to include whole antibodies (e.g., IgG, IgA, IgE, IgM, or IgD), monoclonal antibodies, chimeric antibodies, humanized antibodies, and antibody fragments, including single chain variable fragments (ScFv), single domain antibody, and antigen-binding fragments, genetically engineered antibodies, among others, as long as the characteristic properties (e.g., ability to bind CD30) are retained. The term "antibody fragment" as used herein is intended to include any appropriate antibody fragment that displays antigen binding function, for example, Fab, Fab', F(ab')2, scFv, Fv, dsFv, ds-scFv, Fd, mini bodies, monobodies, and multimers thereof and bispecific antibody fragments. Thus, the bispecific antibodies described herein may be two antibodies that are covalently or non-covalently linked to produce a single bispecific antibody. The two antibodies may be linked by a linker.

As stated above, the term "antibody" includes "antibody fragments" or "antibody-derived fragments" and "antigen binding fragments" which comprise an antigen binding domain. Furthermore, although the two domains of the Fv fragment, VL and VH, are coded for by separate genes, they may be joined, using recombinant methods, by a synthetic linker that enables them to be made as a single protein chain in which the VL and VH regions pair to form monovalent molecules (known as single chain antibodies or single chain Fv (scFv), see for instance Bird et al., Science 242, 423-426 (1988) and Huston et al., PNAS USA 85, 5879-5883 (1988)). Such single chain antibodies are encompassed within the term antibody unless otherwise noted or clearly indicated by context.

Antibodies can be genetically engineered from the CDRs and monoclonal antibody sequences described herein into antibodies and antibody fragments by using conventional techniques such as, for example, synthesis by recombinant techniques or chemical synthesis. Techniques for producing antibody fragments are well known and described in the art.

One may wish to engraft one or more CDRs from the monoclonal antibodies described herein into alternate scaffolds for use in the bispecific antibody. For example, standard molecular biological techniques can be used to transfer the DNA sequences encoding the antibody's CDR(s) to (1) full IgG scaffold of human or other species; (2) a scFv scaffold of human or other species, or (3) other specialty vectors. If the CDR(s) have been transferred to a new scaffold all of the previous modifications described can also be performed. For example, one could consult *Biotechnol Genet Eng Rev*, 2013, 29:175-86 for a review of useful methods.

The bispecific antibodies disclosed in the present invention may be modified to be humanized antibodies which include the constant region from a human germline immunoglobulin sequences. The term "recombinant human antibody" or "humanized antibody" includes all human antibodies that are prepared, expressed, created or isolated by recombinant means, such as antibodies isolated from a host cell such as an SP2-0, NSO or CHO cell (like CHO K1) or from an animal (e.g., a mouse) that is transgenic for human immunoglobulin genes or antibodies or polypeptides expressed using a recombinant expression vector transfected into a host cell. Such recombinant human antibodies have variable and in some embodiments, constant regions derived from human germline immunoglobulin sequences in a rearranged form.

For example, a humanized antibody may comprise the constant regions derived from the human germline immunoglobulin sequence and the "framework" (FR) variable domain residues which are the variable domain residues other than the hypervariable regions (CDRs). The framework of the variable domain usually consists of four FR domains (between the three CDRs, e.g., FR1, FR2, FR3 and FR4) for both the heavy and light chain (e.g., for light chain region would contain: FRL1-CDRL1-FRL2-CDRL2-FRL3-CDRL3-FRL4). Therefore, a humanized antibody may have the constant regions and framework from a human immunoglobulin and the CDRs or hypervariable regions from the mouse monoclonal antibodies described herein.

The term "fragment" as used herein refers to fragments of biological relevance (functional fragment), e.g., fragments which can contribute to or enable antigen binding, e.g., form part or all of the antigen binding site or can contribute to the prevention of the antigen interacting with its natural ligands. Fragments in some embodiments comprise a heavy chain variable region (VH domain) and light chain variable region (VL) of the invention. In some embodiments, the fragments comprise one or more of the heavy chain complementarity determining regions (CDRHs) of the antibodies or of the VH domains, and one or more of the light chain complementarity determining regions (CDRLs), or VL domains to form the antigen binding site. For example, a fragment is suitable for use in the present methods and kits if it retains its ability to bind CD30.

The term "complementarity determining regions" or "CDRs," as used herein, refers to part of the variable chains of immunoglobulins (antibodies) and T cell receptors, generated by B-cells and T-cells respectively, through which these molecules bind to their specific antigen. As the most variable parts of the molecules, CDRs are crucial to the diversity of antigen specificities generated by lymphocytes. There are three CDRs (CDR1, CDR2 and CDR3), arranged non-consecutively, on the amino acid sequence of a variable domain of an antigen binding site. Since the antigen binding sites are typically composed of two variable domains (on two different polypeptide chains, heavy and light chain), there are six CDRs for each antigen binding site that can collectively come into contact with the antigen. A single whole antibody molecule has two antigen binding sites and therefore contains twelve CDRs. Sixty CDRs can be found on a pentameric IgM molecule.

Within the variable domain, CDR1 and CDR2 may be found in the variable (V) region of a polypeptide chain, and CDR3 includes some of V, all of diversity (D, heavy chains only) and joining (J) regions. Since most sequence variation associated with immunoglobulins and T cell receptors is found in the CDRs, these regions are sometimes referred to as hypervariable regions. Among these, CDR3 shows the greatest variability as it is encoded by a recombination of VJ in the case of a light chain region and VDJ in the case of heavy chain regions. The tertiary structure of an antibody is important to analyze and design new antibodies.

As used herein, the terms "proteins" and "polypeptides" are used interchangeably herein to designate a series of amino acid residues connected to the other by peptide bonds between the alpha-amino and carboxy groups of adjacent residues. The terms "protein" and "polypeptide" refer to a polymer of protein amino acids, including modified amino acids (e.g., phosphorylated, glycated, glycosylated, etc.) and amino acid analogs, regardless of its size or function. "Protein" and "polypeptide" are often used in reference to relatively large polypeptides, whereas the term "peptide" is often used in reference to small polypeptides, but usage of these terms in the art overlaps. The terms "protein" and "polypeptide" are used interchangeably herein when referring to an encoded gene product and fragments thereof. Thus, exemplary polypeptides or proteins include gene products, naturally occurring proteins, homologs, orthologs, paralogs, fragments and other equivalents, variants, fragments, and analogs of the foregoing. The antibodies of the present invention are polypeptides, as well the antigen-binding fragments and fragments thereof.

The terms "monoclonal antibody" or "monoclonal antibody composition" as used herein refer to a preparation of antibody molecules of a single amino acid composition that specifically binds to a single epitope of the antigen.

The term "chimeric antibody" refers to an antibody comprising a variable region, i.e., binding region, from one source or species and at least a portion of a constant region derived from a different source or species, usually prepared by recombinant DNA techniques. Other forms of "chimeric antibodies" are those in which the class or subclass has been modified or changed from that of the original antibody. Such "chimeric" antibodies are also referred to as "class-switched antibodies." Methods for producing chimeric antibodies involve conventional recombinant DNA and gene transfection techniques now well known in the art.

In a preferred embodiment, the present disclosure provides a CD30-antibody covalently linked to a CD3 antibody.

CD30 Antibodies or Antigen Binding Fragments Used in the Bispecific Antibodies

The portion of the bispecific antibody that specifically and selectively binds to CD30 may be an antibody, e.g., monoclonal antibody or antigen binding fragment thereof. The CD30 binding antibody or antigen binding fragment thereof is capable of selectively binding to human CD30, and having a different binding specificity to CD30 than the known anti-CD30 antibody AC10 (monoclonal antibody in brentuximab). By "selectively" or "specifically" we mean an antibody capable of binding human CD30 but does not bind to other CD molecules or other cell surface proteins. By binding, we mean that the antibodies are capable of detection at a given tissue's extracellular membrane by standard methods (e.g., tissue section immunofluorescence assays or flow cytometry).

In one embodiment, the CD30 binding portion of the bispecific antibody is a monoclonal antibody (MAbs) that target CD30 and derivatives thereof. Suitable monoclonal antibodies include, but are not limited to, monoclonal antibodies 8D10, 10C2, 12B1, 13H1, and 15B8 produced from hybridoma cell lines as described herein. The monoclonal antibodies used in the bispecific antibodies described herein are able to specifically and selectively bind to CD30 (as demonstrated in FIG. 1). Each of five hybridoma clones, designated as 8D10, 10C2, 12B1, 13H1, and 15B8, bound to CD30+ but not CD30− cell lines indicating specificity for the selected antigen CD30.

In one embodiment, the CD30 binding antibody or antigen binding fragment thereof capable of binding human CD30 comprising, consisting or consisting essentially of: (a) a light chain variable domain comprising a CDRL1 region of SEQ ID NO:2 or a sequence with at least 85% similarity to SEQ ID NO:2, a CDRL2 region of SEQ ID NO:3 or a sequence with at least 85% similarity to SEQ ID NO:3, and a CDRL3 region of SEQ ID NO:4 or a sequence with at least 85% similarity to SEQ ID NO:4 and a heavy chain variable domain comprising a CDRH1 region of SEQ ID NO:6 or a sequence with at least 85% similarity to SEQ ID NO:6, a CDRH2 region of SEQ ID NO:7 or a sequence with at least 85% similarity to SEQ ID NO:7, and a CDRH3 region of SEQ ID NO:8 or a sequence with at least 85% similarity to SEQ ID NO:8; (b) a light chain variable domain comprising a CDRL1 region of SEQ ID NO:10 or a sequence with at least 85% similarity to SEQ ID NO:10, a CDRL2 region of SEQ ID NO:11 or a sequence with at least 85% similarity to SEQ ID NO: 11, and a CDRL3 region of SEQ ID NO:12 or a sequence with at least 85% similarity to SEQ ID NO: 12 and a heavy chain variable domain comprising a CDRH1 region of SEQ ID NO:14 or a sequence with at least 85% similarity to SEQ ID NO:14, a CDRH2 region of SEQ ID NO:15 or a sequence with at least 85% similarity to SEQ ID NO:15 and a CDRH3 region of SEQ ID NO:16 or a sequence with at least 85% similarity to SEQ ID NO:16, (c) a light chain variable domain comprising a CDRL1 region of SEQ ID NO: 18 or a sequence with at least 85% similarity to SEQ ID NO: 18, a CDRL2 region of SEQ ID NO:19 or a sequence with at least 85% similarity to SEQ ID NO:19, and a CDRL3 region of SEQ ID NO:20 or a sequence with at least 85% similarity to SEQ ID NO:20 and a heavy chain variable domain comprising a CDRH1 region of SEQ ID NO:22 or a sequence with at least 85% similarity to SEQ ID NO:22, a CDRH2 region of SEQ ID NO:23 or a sequence with at least 85% similarity to SEQ ID NO:23, and a CDRH3 region of SEQ ID NO:24 or a sequence with at least 85% similarity to SEQ ID NO:24, (d) a light chain variable domain comprising a CDRL1 region of SEQ ID NO:26 or a sequence with at least 85% similarity to SEQ ID NO:26, a CDRL2 region of SEQ ID NO:27 or a sequence with at least 85% similarity to SEQ ID NO:27, and a CDRL3 region of SEQ ID NO:28 or a sequence with at least 85% similarity to SEQ ID NO:28 and a heavy chain variable domain comprising a CDRH1 region of SEQ ID NO:30 or a sequence with at least 85% similarity to SEQ ID NO:30, a CDRH2 region of SEQ ID NO:31 or a sequence with at least 85% similarity to SEQ ID NO:31, and a CDRH3 region of SEQ ID NO:32 or a sequence with at least 85% similarity to SEQ ID NO:32, or (e) a light chain variable domain comprising a CDRL1 region of SEQ ID NO:34 or a sequence with at least 85% similarity to SEQ ID NO:34 or a sequence with at least 85% similarity to SEQ ID NO:34, a CDRL2 region of SEQ ID NO:35 or a sequence with at least 85% similarity to SEQ ID NO:35, and a CDRL3 region of SEQ ID NO:36 or a sequence with at least 85% similarity to SEQ ID NO:36 and a heavy chain variable domain comprising a CDRH1 region of SEQ ID NO:38 or a sequence with at least 85% similarity to SEQ ID NO:38, a CDRH2 region of SEQ ID NO:39 or a sequence with at least 85% similarity to SEQ ID NO:39, and a CDRH3 region of SEQ ID NO:40 or a sequence with at least 85% similarity to SEQ ID NO:40.

In another embodiment, the CD30 binding antibody or antigen binding fragment thereof capable of binding human CD30 comprising, consisting or consisting essentially of: a heavy and a light chain, wherein the antigen binding domain formed by the heavy and light chain is able to bind specifically to human CD30.

In one embodiment, the anti-CD30 antibody or antigen-binding fragment thereof comprises, consists essentially of or consists of a light chain comprising SEQ ID NO: 1 or a sequence with at least 85% similarity to SEQ ID NO: 1, and a heavy chain comprising SEQ ID NO:5 or a sequence with at least 85% similarity to SEQ ID NO:5.

In another embodiment, the isolated anti-CD30 antibody or antigen-binding fragment thereof comprises, consists essentially of or consists of a light chain comprising SEQ ID NO:9 or a sequence with at least 85% similarity to SEQ ID NO:9, and a heavy chain comprising SEQ ID NO:13 or a sequence with at least 85% similarity to SEQ ID NO:13.

In another embodiment, the isolated anti-CD30 antibody or antigen-binding fragment thereof comprises, consists essentially of or consists of a light chain comprising SEQ ID NO:17 or a sequence with at least 85% similarity to SEQ ID NO:17, and a heavy chain comprising SEQ ID NO:21 or a sequence with at least 85% similarity to SEQ ID NO:21.

In another embodiment, the isolated anti-CD30 or antigen-binding fragment thereof comprises, consists essentially of or consists of a light chain comprising SEQ ID NO:25 or a sequence with at least 85% similarity to SEQ ID NO:25, and a heavy chain comprising SEQ ID NO:29 or a sequence with at least 85% similarity to SEQ ID NO:29; and In another embodiment, the isolated anti-CD30 antibody or antigen-binding fragment thereof comprises, consists essentially of or consists of a light chain comprising SEQ ID NO:33 or a sequence with at least 85% similarity to SEQ ID NO:33, and a heavy chain comprising SEQ ID NO:37 or a sequence with at least 85% similarity to SEQ ID NO:37.

In one embodiment, the CD30 binding antibody or antigen binding fragment thereof capable of binding human CD30 comprising, consisting or consisting essentially of: (a) a light chain variable domain comprising a CDRL1 region of SEQ ID NO:2, a CDRL2 region of SEQ ID NO:3, and a CDRL3 region of SEQ ID NO:4 and a heavy chain variable domain comprising a CDRH1 region of SEQ ID NO:6, a CDRH2 region of SEQ ID NO:7, and a CDRH3 region of SEQ ID NO:8; (b) a light chain variable domain comprising a CDRL1 region of SEQ ID NO:10, a CDRL2 region of SEQ ID NO:11, and a CDRL3 region of SEQ ID NO: 12 and a heavy chain variable domain comprising a CDRH1 region of SEQ ID NO: 14, a CDRH2 region of SEQ ID NO: 15 and a CDRH3 region of SEQ ID NO: 16, (c) a light chain variable domain comprising a CDRL1 region of SEQ ID NO:18, a CDRL2 region of SEQ ID NO: 19, and a CDRL3 region of SEQ ID NO:20 and a heavy chain variable domain comprising a CDRH1 region of SEQ ID NO:22, a CDRH2 region of SEQ ID NO:23, and a CDRH3 region of SEQ ID NO:24, (d) a light chain variable domain comprising a CDRL1 region of SEQ ID NO:26, a CDRL2 region of SEQ ID NO:27, and a CDRL3 region of SEQ ID NO:28 and a heavy chain variable domain comprising a CDRH1 region of SEQ ID NO:30, a CDRH2 region of SEQ ID NO:31, and a CDRH3 region of SEQ ID NO:32, or (e) a light chain variable domain comprising a CDRL1 region of SEQ ID NO:34, a CDRL2 region of SEQ ID NO:35, and a CDRL3 region of SEQ ID NO:36 and a heavy chain variable domain comprising a CDRH1 region of SEQ ID NO:38, a CDRH2 region of SEQ ID NO:39, and a CDRH3 region of SEQ ID NO:40.

In one embodiment, the anti-CD30 antibody is monoclonal antibody 8D10. In another embodiment, the anti-CD30 antibody is monoclonal antibody 10C2. In another embodiment, the anti-CD30 antibody is monoclonal antibody 12B1. In another embodiment, the anti-CD30 antibody is monoclonal antibody 13H1. In another embodiment, the anti-CD30 antibody is monoclonal antibody 15B8. In a preferred embodiment, the anti-CD30 antibody is monoclonal antibody 8D10 or 10C2.

In some embodiments, the anti-CD30 antibody or antigen-binding fragment thereof is selected from the group consisting of a monoclonal antibody, a humanized antibody, a single chain variable fragment (scFv) antibody, a single domain antibody, an antigen-binding fragment and a chimeric antibody.

In some embodiments, the antibodies comprise a light and a heavy chain that have substantial identity to the polypeptide sequences found in SEQ ID NOs: 1 and 5, 9 and 13, 17 and 21, 25 and 29, 33 and 37 respectively, or substantial identity in the CDR regions within the heavy and light chain of the antibody or antigen-binding fragment thereof as described herein.

In some embodiments, the antibodies have at least 85% identity to the light chain and heavy chain found in SEQ ID NOs:1 and 5, 9 and 13, 17 and 21, 25 and 29, 33 and 37 respectively, alternatively at least 90% sequence identity to the light chain and heavy chain found in SEQ ID NOs:1 and 5, 9 and 13, 17 and 21, 25 and 29, 33 and 37 respectively, alternatively at least 95% sequence identity to the light chain and heavy chain found in SEQ ID NOs:1 and 5, 9 and 13, 17 and 21, 25 and 29, 33 and 37 respectively, alternatively at least 97% sequence identity to the light chain and heavy chain found in SEQ ID NOs: 1 and 5, 9 and 13, 17 and 21, 25 and 29, 33 and 37 respectively, alternatively at least 98% sequence identity to the light chain and heavy chain found in SEQ ID NOs:1 and 5, 9 and 13, 17 and 21, 25 and 29, 33 and 37 respectively, alternatively at least 100% sequence identity to the light chain and heavy chain found in SEQ ID NOs:1 and 5, 9 and 13, 17 and 21, 25 and 29, 33 and 37 respectively.

In some embodiments, the antibodies have at least 85% identity to the CDR domains described herein, alternatively at least 90% sequence identity, alternatively at least 95% sequence identity, alternatively at least 97% sequence identity, alternatively at least 98% sequence identity, alternatively at least 100% sequence identity. In some embodiments, the antibody or antigen binding fragment thereof has at least 85-100% sequence identity within CDRH1, CDRH2 and CDRH3 within SEQ ID NO:5 (e.g., SEQ ID Nos. 6-8), SEQ ID NO:13 (e.g., SEQ ID Nos: 14-16), SEQ ID NO:21 (e.g., SEQ ID Nos: 22-24), SEQ ID NO:29 (e.g., SEQ ID Nos: 30-32), or SEQ ID NO:37 (e.g., SEQ ID NOS: 38-40) and/or at least 85%-100% sequence identity within CDRL1, CDRL2 and CDRL3 within SEQ ID NO:1 (e.g. SEQ ID Nos. 2-4), SEQ ID NO:9 (e.g., SEQ ID Nos: 10-12), SEQ ID NO:17 (e.g., SEQ ID NOs. 18-20), SEQ ID NO:25 (e.g., SEQ ID Nos: 26-28), or SEQ ID NO:33 (e.g., SEQ ID Nos: 34-36).

In one embodiment, the antibody or antigen binding fragment thereof has at least 95-100% sequence identity within CDRH1, CDRH2 and CDRH3 within SEQ ID NO:5 (e.g., SEQ ID Nos. 6-8), SEQ ID NO:13 (e.g., SEQ ID Nos: 14-16), SEQ ID NO:21 (e.g., SEQ ID Nos: 22-24), SEQ ID NO:29 (e.g., SEQ ID Nos: 30-32), or SEQ ID NO:37 (e.g., SEQ ID NOS: 38-40) and/or at least 95%-100% sequence identity within CDRL1, CDRL2 and CDRL3 within SEQ ID NO:1 (e.g. SEQ ID Nos. 2-4), SEQ ID NO:9 (e.g., SEQ ID Nos: 10-12), SEQ ID NO:17 (e.g., SEQ ID NOs. 18-20), SEQ ID NO:25 (e.g., SEQ ID Nos: 26-28), or SEQ ID NO:33 (e.g., SEQ ID Nos: 34-36).

In one embodiment, the antibody or antigen binding fragment thereof has 100% sequence identity within CDRH1, CDRH2 and CDRH3 within SEQ ID NO:5 (e.g., SEQ ID Nos. 6-8), SEQ ID NO:13 (e.g., SEQ ID Nos: 14-16), SEQ ID NO:21 (e.g., SEQ ID Nos: 22-24), SEQ ID NO:29 (e.g., SEQ ID Nos: 30-32), or SEQ ID NO:37 (e.g., SEQ ID NOS: 38-40) and/or 100% sequence identity within CDRL1, CDRL2 and CDRL3 within SEQ ID NO: 1 (e.g. SEQ ID Nos. 2-4), SEQ ID NO:9 (e.g., SEQ ID Nos: 10-12), SEQ ID NO:17 (e.g., SEQ ID NOs. 18-20), SEQ ID NO:25 (e.g., SEQ ID Nos: 26-28), or SEQ ID NO:33 (e.g., SEQ ID Nos: 34-36).

T Cell or NK Surface Antigen Antibodies or Antigen Binding Fragments Used in the Bispecific Antibodies The portion of the bispecific antibody that specifically and selectively binds to T cell or NK cell surface may be an antibody, e.g., monoclonal antibody or antigen binding fragment thereof. T cell surface markers are known in the art and include, but are not limited to, for example, CD3. In one embodiment, the suitable anti-T cell surface antibodies are known in the art and include, but are not limited to, e.g., anti-CD3 antibody or antigen binding fragment thereof. Suitably, the anti-T cell surface antibody is an anti-CD3 antibody.

The anti-CD3 antibody to be used in the present invention may be any antibody as long as it is specific for CD3. The CD3 antibody may be a CD3 monoclonal antibody, for example OKT3. OKT3, a murine IgG2a mAb directed against the ε-chain of the CD3 complex on human T lymphocytes (Salmeron et al., J. Immunol. 147 (1991), 3047-3052) and produced by a hybridoma with the ATCC deposit number of CRL 8001.

The NK cell surface antigen may by an NK surface antigen known in the art, for example, CD16. In one embedment, a bispecific antibody comprising an anti-CD30 antibody described herein and an anti-CD16 antibody or antigen binding fragment thereof is contemplated.

The polypeptide and nucleic acids described herein encompass those to which conservative modifications have been made. The terms "conservative modification" or "conservative sequence modification" refer to an amino acid modification that does not significantly alter the binding characteristics of an antibody or antibody fragment containing an amino acid sequence. Such conservative modifications include amino acid substitutions, additions and deletions. Modifications can be introduced into the antibodies or antibody fragments of the present invention by standard techniques known in the art, such as site-directed mutagenesis and PCR-mediated mutagenesis. Conservative amino acid substitutions are those in which the amino acid residue is replaced by an amino acid residue having a similar side chain. Families of amino acid residues having similar side chains have been defined in the related art. These families include, but are not limited to, basic side chains (e.g., lysine (Lys, L), arginine (Arg), histidine (His, H); acidic side chains (e.g., aspartic acid (Asp, D), glutamic acid (Glu, E)), uncharged polar side chains (e.g., asparagine (Asn, N), glutamine (Gln, Q), serine (Ser, S), threonine (Thr, T), tyrosine (Tyr, Y), nonpolar side chains (e.g., alanine (Ala, A), valine (Val, V), leucine (Leu, L), isoleucine (Ile, I), proline (Pro, P), phenylalanine (Phe, F), methionine (Met, M), Glycine (Gly, G), Cysteine (Cys, C)), beta-branched side chains (e.g., leucine (L), valine (V), isoleucine (I)). Thus, one or more amino acid residues within the antibody or antigen binding fragment thereof of the present invention may be replaced by other amino acid residues from the same side chain family, and the altered antibodies or antibody fragments thereof may be tested using the functional assays described herein. Suitably, conservative changes may even be made in the CDR region and not alter the functional binding of the antibody or antigen binding fragment thereof, which can be tested by the methods described herein.

Protein and nucleic acid sequence identities are evaluated using the Basic Local Alignment Search Tool ("BLAST") which is well known in the art (Karlin and Altschul, 1990, *Proc. Natl. Acad. Sci. USA* 87: 2267-2268; Altschul et al., 1997, *Nucl. Acids Res.* 25: 3389-3402). The BLAST programs identify homologous sequences by identifying similar segments, which are referred to herein as "high-scoring segment pairs," between a query amino or nucleic acid sequence and a test sequence which is known or obtained from a protein or nucleic acid sequence database. Preferably, the statistical significance of a high-scoring segment pair is evaluated using the statistical significance formula (Karlin and Altschul, 1990), the disclosure of which is incorporated by reference in its entirety. The BLAST programs can be used with the default parameters or with modified parameters provided by the user.

"Percentage of sequence identity" or "sequence similarity" is determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The term "substantial identity" of polynucleotide sequences means that a polynucleotide comprises a sequence that has at least 85% sequence identity. Alternatively, percent identity can be any integer from 75% to 100%. More preferred embodiments include at least: 75%, 80%, 85%, 86%, 87%, 88%, 89%, 90%, 91%, 92%, 93%, 94%, 95%, 96%, 97%, 98% or 99% compared to a reference sequence using the programs described herein; preferably BLAST using standard parameters, as described. These values can be appropriately adjusted to determine corresponding identity of proteins encoded by two nucleotide sequences by taking into account codon degeneracy, amino acid similarity, reading frame positioning and the like.

"Substantial identity" of amino acid sequences for purposes of this invention normally means polypeptide sequence identity of at least 85%. Preferred percent identity of polypeptides can be any integer from 85% to 100%. More preferred embodiments include at least 85%, 86%, 87%, 88%, 89%, 90%, 91%, 92%, 93%, 94%, 95%, 96%, 97%, 98%, or 99%.

One may wish to express the bispecific antibody as a fusion protein linking the anti-CD30 antibody to the anti-T cell surface antigen antibody (e.g., anti-CD3 antibody). For example, one may wish to express the bispecific antibody of the present invention with a protein linker between the two antibodies. Standard molecular biology techniques (e.g., restriction enzyme based sub-cloning, or homology based sub-cloning) could be used to place the DNA sequence encoding the first anti-CD30 antibody in frame with the second anti-CD3 antibody to form a single bispecific antibody. The fusion protein is then produced as one peptide in a host cell (e.g., yeast, bacteria, insect, or mammalian cell) and purified before use. Note the therapeutic does not need to be a whole protein. For example, it can be a single peptide chain comprising the VH and VL sequences of the CD30 antibody linked to the VH and VL sequences of the CD3 antibody.

Making of Bispecific Antibodies

Conventional linking methods of linking polypeptides, in particular an antibody, are known in the art (e.g., See TERNYNCK and AVRAMEAS, 1987, "Techniques immunoenzymatiques" Ed. INSERM, Paris or G. T. Hermanson, Bioconjugate Techniques, 2010, Academic Press). Many chemical cross-linking methods are also known in the art. Cross-linking reagents may be homobifunctional (i.e., having two functional groups that undergo the same reaction) or heterobifunctional (i.e., having two different functional groups). Numerous cross-linking reagents are commercially available. Detailed instructions for their use are readily available from the commercial suppliers. A general reference on polypeptide cross-linking and conjugate preparation is: WONG, Chemistry of protein conjugation and cross-linking, CRC Press (1991).

Figures 14A, 14B:
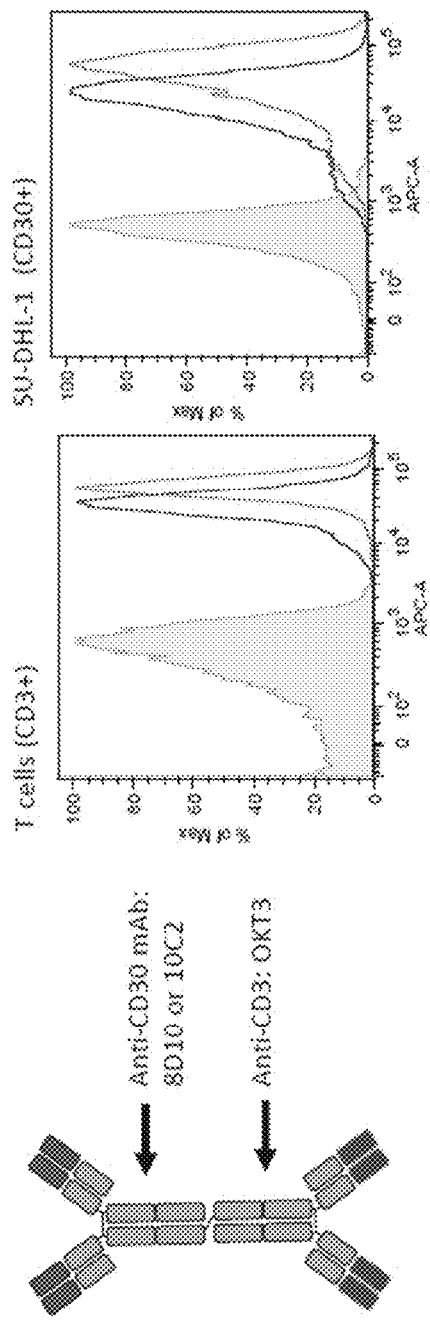
FIGS. 14A-14E shows further characterization of the bispecific antibodies.
Figure 14C:
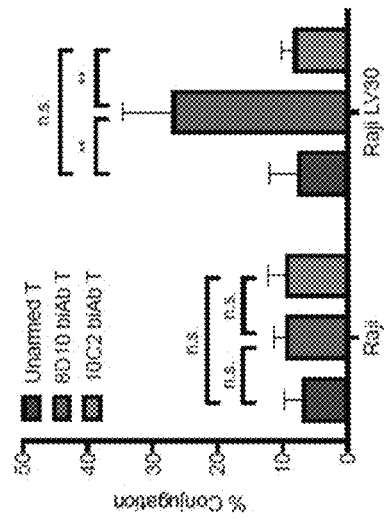
Figure 14D:
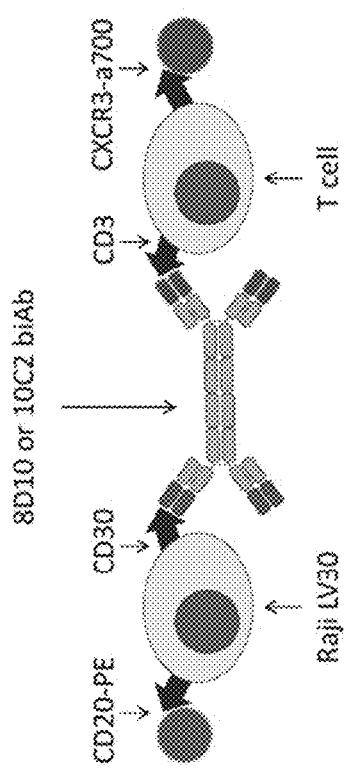
Figure 14E:
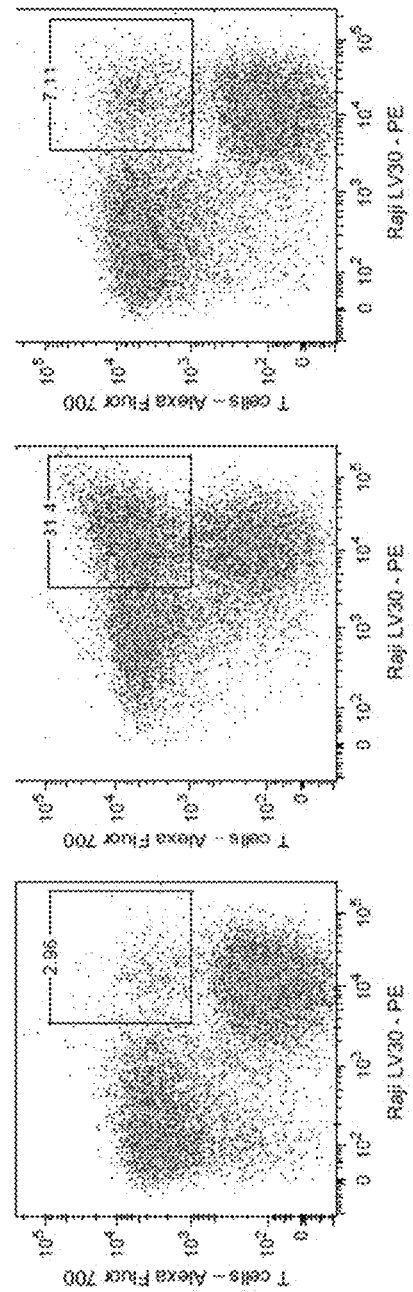
Figure 14F:
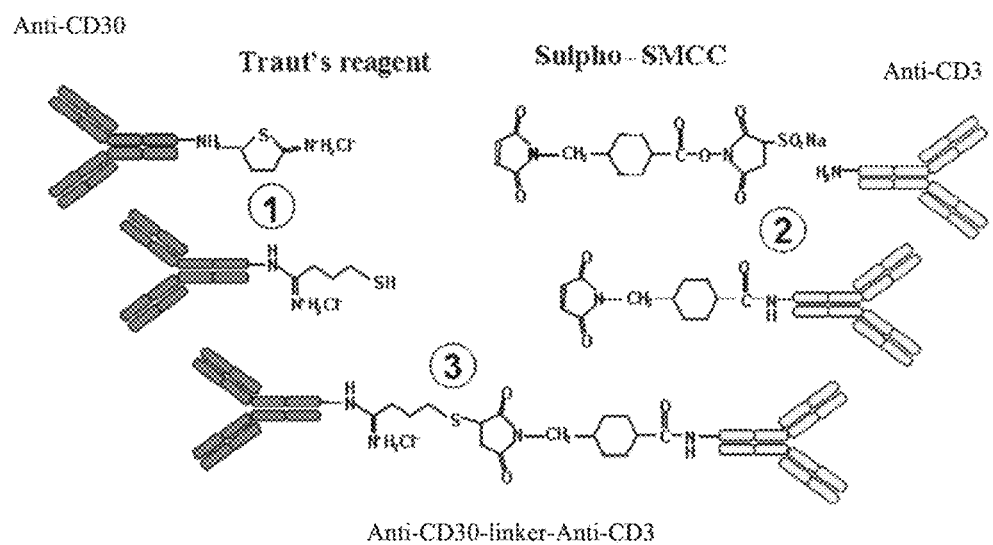
FIG. 14F is an example method of conjugating the CD30+ antibody and CD3 antibody of the present invention.
Figure 15:
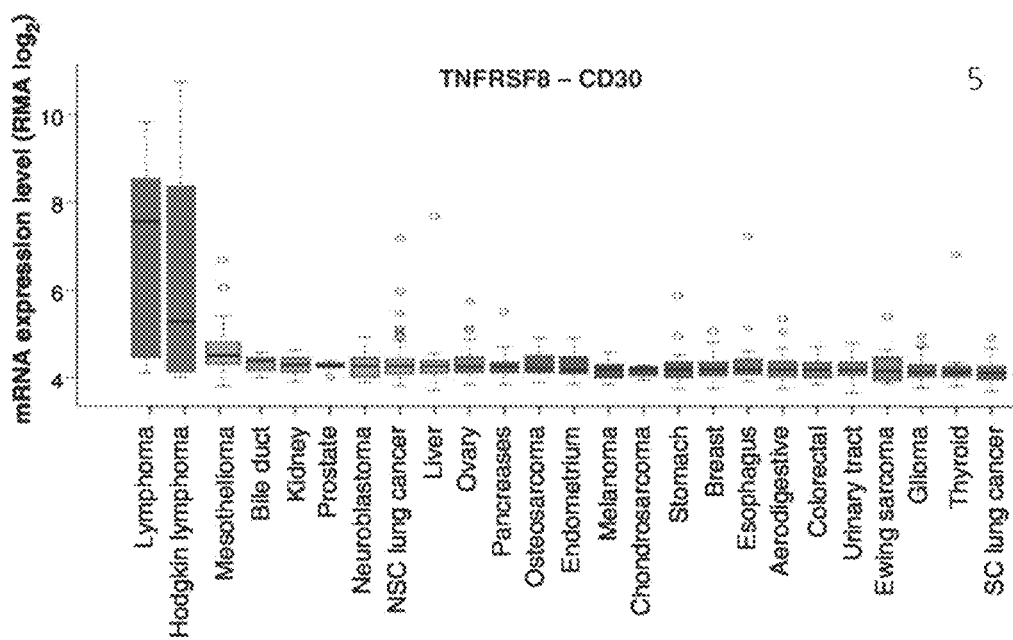
FIG. 15 shows the expression of CD30 on tumor cells.
Figure 16A:
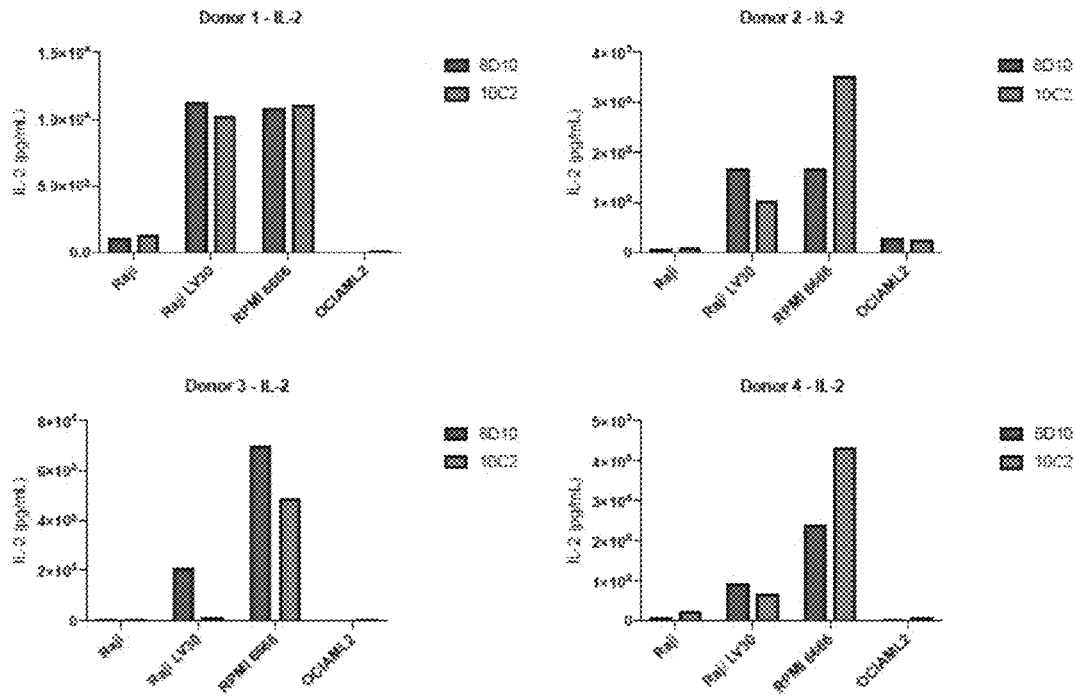
FIGS. 16A-16B are bar graphs depicting cytokines produced by biAb-armed T cells. 8D10 biAb or 10C2 biAb-armed T cells produce the pro-inflammatory cytokines IL-2 (FIG. 16A) and IFN-γ (FIG. 16B) when co-cultured with CD30+ tumor cells, indicating that binding of T cells to the biAb is sufficient to trigger T cell activation and cytotoxicity. Armed T cells cocultured with CD30– cells have much lower cytokine production demonstrating the specificity of this approach.
Figure 16B:
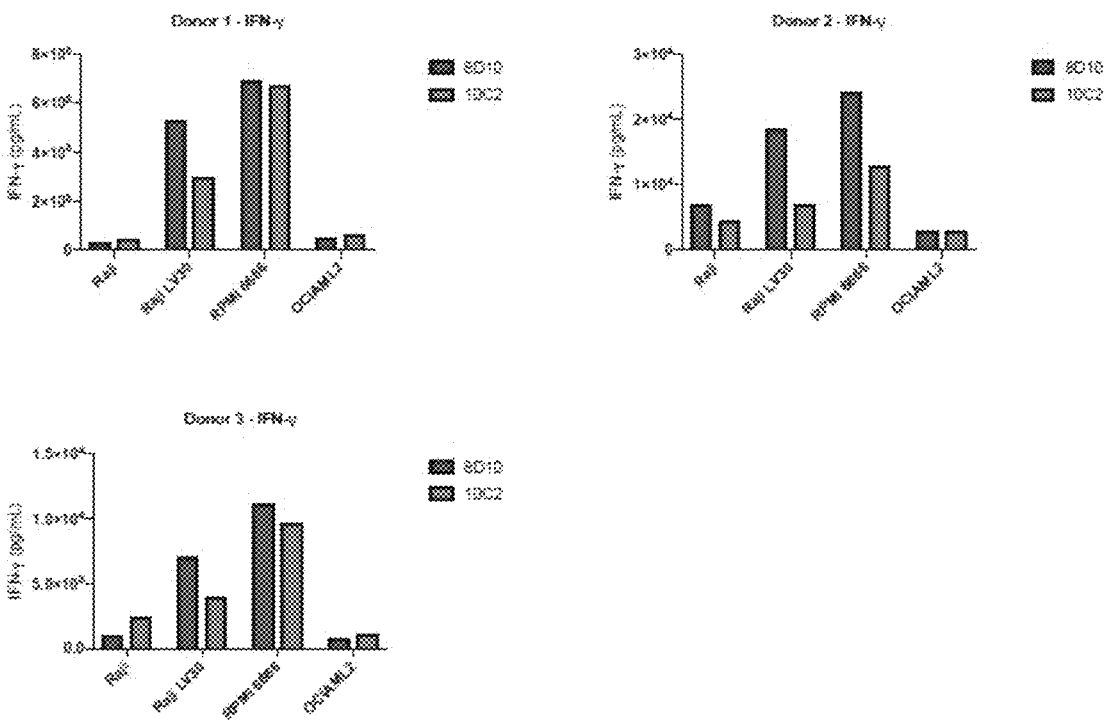

The anti-CD30 and anti-T cell/NK cell antibody (e.g., anti-CD3 antibody) may be covalently linked as depicted in FIGS. 14A-14F and as described in "CD20-Targeted T Cells after Stem Cell Transplantation for High Risk and Refractory Non-Hodgkin's Lymphoma" Lum, Lawrence G. et al., Biology of Blood and Marrow Transplantation, Volume 19, Issue 6, 925-933, incorporated by reference in its entirety. Briefly, the process of heteroconjugation of anti-CD3 with anti-CD30 antibody is shown in FIGS. 14A-14F. FIG. 14A shows one embodiment of how the antibodies may be conjugated together, by the end of the Fc portions. FIG. 14B shows a model method of covalently linking the antibodies. Step 1 shows cross-linking of Traut's reagent to anti-CD3 (OKT3) mAb and the cross-linking of Sulpho-SMCC to anti-CD30; step 2 shows the heteroconjugation of the cross-linked anti-CD3 with the cross-linked anti-CD30; and step 3 shows formation of anti-CD3-anti-CD20 BiAb (CD30Bi).

Other suitable methods of covalently linking two antibodies or antigen binding fragments thereof are known in the art. For example, the bispecific antibodies of the invention can be produced by a process in which two immunoglobulin molecules are linked together using a cross linking agent such as N-succinimidyl 3-(2-pyridyldithiol)-propionate, S-acetylmercaptosuccinic acid anhydride or the like (J. Exp. Med., 163, 166 (1986)) or by a process in which Fab fragments of immunoglobulin molecules are linked together (Eur. J. Immunol., 19, 1437 (1989)).

Methods of preparing bispecific antibodies of the present invention include those described in WO 2008119353 (Genmab), WO 2011131746 (Genmab) and reported by van der Neut-Kolfschoten et al. (Science. 2007 Sep. 14; 317 (5844): 1554-7). Examples of other platforms useful for preparing bispecific antibodies include but are not limited to BiTE (Micromet), DART (MacroGenics), Fcab and Mab2 (F-star), Fc-engineered IgG1 (Xencor) or DuoBody (based on Fab arm exchange, Genmab).

In addition, methods such as the hybrid hybridoma and chemical conjugation methods (Marvin and Zhu (2005) Acta Pharmacol Sin 26: 649) can also be used. Co-expression in a host cell of two antibodies, consisting of different heavy and light chains, leads to a mixture of possible antibody products in addition to the desired bispecific antibody, which can then be isolated by, e.g., affinity chromatography or similar methods.

Strategies favoring the formation of a functional bispecific, product, upon co-expression of different antibody constructs can also be used, e.g., the method described by Lindhofer et al. (1995 J Immunol 155: 219). Fusion of rat and mouse hybridomas producing different antibodies leads to a limited number of heterodimeric proteins because of preferential species-restricted heavy/light chain pairing. Another strategy to promote formation of heterodimers over homodimers is a "knob-into-hole" strategy in which a protuberance is introduced on a first heavy-chain polypeptide and a corresponding cavity in a second heavy-chain polypeptide, such that the protuberance can be positioned in the cavity at the interface of these two heavy chains so as to promote heterodimer formation and hinder homodimer formation. "Protuberances" are constructed by replacing small amino-acid side-chains from the interface of the first polypeptide with larger side chains. Compensatory "cavities" of identical or similar size to the protuberances are created in the interface of the second polypeptide by replacing large amino-acid side-chains with smaller ones (U.S. Pat. No. 5,731,168). EP1870459 (Chugai) and WO 2009089004 (Amgen) describe other strategies for favoring heterodimer formation upon co-expression of different antibody domains in a host cell. In these methods, one or more residues that make up the CH3-CH3 interface in both CH3 domains are replaced with a charged amino acid such that homodimer formation is electrostatically unfavorable and heterodimerization is electrostatically favorable. WO2007110205 (Merck) describe yet another strategy, wherein differences between IgA and IgG CH3 domains are exploited to promote heterodimerization.

Another in vitro method for producing bispecific antibodies has been described in WO 2008119353 (Genmab), wherein a bispecific antibody is formed by "Fab-arm" or "half-molecule" exchange (swapping of a heavy chain and attached light chain) between two monospecific IgG4- or IgG4-like antibodies upon incubation under reducing conditions. The resulting product is a bispecific antibody having two Fab arms which may comprise different sequences.

Further embodiments provide an isolated nucleic acid that encodes for the bispecific antibodies or antigen binding fragment thereof described above. Some embodiments provide an isolated polynucleotide encoding a bispecific antibody described herein. As used herein, term "nucleic acid" or "polynucleotide" refers to deoxyribonucleic acids (DNA) or ribonucleic acids (RNA) and polymers thereof in either single- or double-stranded form. Unless specifically limited, the term encompasses nucleic acids containing known analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), alleles, orthologs, SNPs, and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., Nucleic Acid Res. 19:5081 (1991); Ohtsuka et al., J. Biol. Chem. 260: 2605-2608 (1985); and Rossolini et al., Mol. Cell. Probes 8:91-98 (1994)).

A recombinant expression cassette comprising a polynucleotide encoding the bispecific antibody or antigen binding fragment thereof of the present invention is also contemplated. The polynucleotide may be under the control of a transcriptional promoter allowing the regulation of the transcription of said polynucleotide in a host cell. Said polynucleotide can also be linked to appropriate control sequences allowing the regulation of its translation in a host cell.

The present invention also provides a expression vector or recombinant vector (e.g., a recombinant expression vector) comprising a polynucleotide encoding the bispecific antibodies according to the present invention. Advantageously, said recombinant expression vector is a recombinant expression vector comprising an "expression cassette" or "expression construct" according to the present invention. With the construct, the polynucleotides may operatively linked to a transcriptional promoter (e.g., a heterologous promoter) allowing the construct to direct the transcription of said polynucleotide in a host cell. Such vectors are referred to herein as "recombinant constructs," "expression constructs," "recombinant expression vectors" (or simply, "expression vectors" or "vectors").

The term vector includes a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. One type of vector is a "plasmid", which refers to a circular double stranded DNA loop into which additional DNA segments may be ligated, specifically exogenous DNA segments encoding the antibodies or fragments thereof. Another type of vector is a viral vector, wherein additional DNA segments may be ligated into the viral genome. Certain vectors are capable of autonomous replication in a host cell into which they are introduced. Other vectors can be integrated into the genome of a host cell upon introduction into the host cell, and thereby are replicated along with the host genome (e.g. lentiviral vectors). Vector includes expression vectors, such as viral vectors (e.g., replication defective retroviruses (including lentiviruses), adenoviruses and adeno-associated viruses (rAAV)), which serve equivalent functions. One type of vector is a "plasmid", which refers to a circular double stranded DNA loop into which additional DNA segments may be ligated, specifically exogenous DNA segments encoding the antibodies or fragments thereof. Another type of vector is a viral vector, wherein additional DNA segments may be ligated into the viral genome. Certain vectors are capable of autonomous replication in a host cell into which they are introduced. Other vectors can be integrated into the genome of a host cell upon introduction into the host cell, and thereby are replicated along with the host genome (e.g. lentiviral vectors). Vector includes expression vectors, such as viral vectors (e.g., replication defective retroviruses (including lentiviruses), adenoviruses and adeno-associated viruses (rAAV)), which serve equivalent functions.

The present invention also provides a host cell able to express the bispecific antibody described herein. In one embodiment, the host cell is a fused hybridoma cell of two hydridoma cells. In another embodiment, the host cell contains isolated nucleic acids or a recombinant expression cassette or a recombinant expression vector according to the present invention able to express the bispecific antibody. The host cell can be a prokaryotic or eukaryotic host cell. The host cell is capable of expressing the bispecific antibodies of the present invention. Suitable host cells include, but are not limited to, mammalian cells, bacterial cells and yeast cells. In some embodiments, the host cell may be a eukaryotic cell. The terms "host cell" also includes a cell into which exogenous nucleic acid has been introduced, including the progeny of such cells. Host cells include "transformants" and "transformed cells", which include the primar transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

In other embodiments, the invention includes a purified and isolated host cell comprising an expression vector containing an isolated nucleic acid capable of encoding the bispecific antibody. It should be appreciated that the host cell can be any cell capable of expressing antibodies, for example fungi; mammalian cells; insect cells, using, for example, a baculovirus expression system; plant cells, such as, for example, corn, rice, *Arabidopsis*, and the like. See, generally, Verma, R. et al., *J Immunol Methods*. 1998 Jul. 1; 216(1-2):165-81.

The bispecific can be wholly or partially synthetically produced that are used to make the bispecific antibody. Thus the antibody may be from any appropriate source, for example recombinant sources and/or produced in transgenic animals or transgenic plants. Thus, the bispecific antibody molecules can be produced in vitro or in vivo. Preferably the anti-CD30 or anti-CD3 antibody or antibody fragment comprises at least the heavy chain variable region (VH) which generally comprises the antigen binding site. In preferred embodiments, the antibody or antibody fragment comprises the heavy chain variable region and light chain variable region (VL). The bispecific antibody comprising the antibody or antibody fragment can be made that comprises all or a portion of a heavy chain constant region, such as an IgG1, IgG2, IgG3, IgG4, IgA1, IgA2, IgE, IgM or IgD constant region.

Furthermore, the antibody or antibody fragment can comprise all or a portion of a kappa light chain constant region or a lambda light chain constant region. All or part of such constant regions may be produced wholly or partially synthetic. Appropriate sequences for such constant regions are well known and documented in the art.

In some embodiments, the disclosure provides a pharmaceutical composition comprising the isolated bispecific antibody or antigen binding fragment thereof specific for human CD30 and a T cell surface antigen (e.g., CD3). In a preferred embodiment, the composition further includes a suitable carrier, preferably a pharmaceutically acceptable carrier. Compositions are provided that include one or more of the disclosed bispecific antibodies. The compositions can be prepared in unit dosage forms for administration to a subject. The amount and timing of administration are at the discretion of the treating clinician to achieve the desired outcome. The bispecific antibody can be formulated for systemic or local (such as intravenous, intrathecal) administration.

As used herein, "pharmaceutical composition" means therapeutically effective amounts of the antibody together with a pharmaceutically-acceptable carrier. "Pharmaceutically acceptable" carriers are known in the art and include, but are not limited to, for example, suitable diluents, preservatives, solubilizers, emulsifiers, liposomes, nanoparticles and adjuvants. Pharmaceutically acceptable carriers are well known to those skilled in the art and include, but are not limited to, 0.01 to 0.1 M and preferably 0.05M phosphate buffer or 0.9% saline. Additionally, such pharmaceutically acceptable carriers may be aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include isotonic solutions, alcoholic/aqueous solutions, emulsions or suspensions, including saline and buffered media.

Pharmaceutical compositions of the present disclosure may include liquids or lyophilized or otherwise dried formulations and may include diluents of various buffer content (e.g., Tris-HCl, acetate, phosphate), pH and ionic strength, additives such as albumin or gelatin to prevent absorption to surfaces, detergents (e. g., Tween 20, Tween 80, Pluronic F68, bile acid salts), solubilizing agents (e.g., glycerol, polyethylene glycerol), anti-oxidants (e.g., ascorbic acid, sodium metabisulfite), preservatives (e.g., Thimerosal, benzyl alcohol, parabens), bulking substances or tonicity modifiers (e.g., lactose, mannitol), covalent attachment of polymers such as polyethylene glycol to the protein, complexation with metal ions, or incorporation of the material into or onto particulate preparations of polymeric compounds such as polylactic acid, polyglycolic acid, hydrogels, etc, or onto liposomes, microemulsions, micelles, milamellar or multilamellar vesicles, erythrocyte ghosts, or spheroplasts. Such compositions will influence the physical state, solubility, stability, rate of in vivo release, and rate of in vivo clearance. Controlled or sustained release compositions include formulation in lipophilic depots (e.g., fatty acids, waxes, oils).

In some embodiments, the compositions comprise a pharmaceutically acceptable carrier, for example, buffered saline, and the like. The compositions can be sterilized by conventional, well known sterilization techniques. The compositions may contain pharmaceutically acceptable additional substances as required to approximate physiological conditions such as a pH adjusting and buffering agent, toxicity adjusting agents, such as, sodium acetate, sodium chloride, potassium chloride, calcium chloride, sodium lactate, and the like.

In some embodiments, the antibodies are provided in lyophilized form and rehydrated with sterile water or saline solution before administration. In some embodiments, the antibodies are provided in sterile solution of known concentration. In some embodiments, the antibody composition may be added to an infusion bag containing 0.9% sodium chloride, USP and in some cases, administered in a dosage of from 0.5 to 15 mg/kg of body weight.

Methods of Use

The bispecific antibodies described herein are able to stimulate a T cell or NK cell response to a specific CD30+ tumor cell. The bispecific antibody bring T-cell via its CD3 receptor into close contact with the tumor cell (via its CD30 antigen) to form an immunological synapse, which generates a strong activating signal cell mediated signal. The bispecific antibody allows the T-cells to be activated at the site of tumor cells allowing for a T-cell mediated response against the CD30+ tumor cell.

In one embodiment, this activating signal induces the transport of cytotoxic granules to the cell surface where they release perforin and granzyme in the vicinity of the tumor cell. For example, granules containing cell lysing components, such as perforin, granzyme and lysosomal enzymes, are transported towards the cell membrane of the T-cell. Once at the surface and subsequently secreted into the extracellular matrix. Perforin causes the formation of pores in the target cell, thereby facilitating the entry of the cell lysing components. This set of activities leads to tumor cell apoptosis.

In another embodiment, the present disclosure provides a method of inhibiting or reducing growth of a tumor cell expressing CD30, comprising contacting the tumor cell with an effective amount of the bispecific antibody of such that the growth of the cell is inhibited. In some embodiments, inhibiting cell growth includes killing or apoptosising the cancer cell. In some embodiments, the method includes reducing, inhibiting or preventing growth of tumor cells.

As used herein, the term "inhibits proliferation" (e.g. referring to cells, such as tumor cells) is intended to include any substantial decrease in the cell proliferation when contacted with a bispecific antibody as compared to the proliferation of the same cells not in contact with the bispecific antibody, e.g., the inhibition of proliferation of a cell culture by at least about 10%, at least about 20% or at least about 30%.

In some embodiments, the antibodies of the invention specifically bind CD30 and T cells (via CD3) and exert cytostatic and cytotoxic effects on malignant cells in cancer (e.g., Hodgkin's lymphoma).

One embodiment of the present invention provides a method of treating a patient having a CD30+ cancer, the method comprising administering a therapeutically effective amount of the isolated bispecific antibody described herein capable of simultaneously binding human CD30 and T cell surface antigen as described herein to treat the cancer.

For purposes of the present invention, "treating" or "treatment" describes the management and care of a subject for the purpose of combating the disease, condition, or disorder. Treating includes the administration of an antibody of present invention to prevent the onset of the symptoms or complications, alleviating the symptoms or complications, or eliminating the disease, condition, or disorder.

The term "treating" can be characterized by one or more of the following: (a) the reducing, slowing or inhibiting the growth of cancer, including reducing slowing or inhibiting the growth of cancer cells; (b) preventing the further growth of tumors; (c) reducing or preventing the metastasis of cancer within a patient, and (d) reducing or ameliorating at least one symptom of the cancer. In some embodiments, the optimum effective amounts can be readily determined by one of ordinary skill in the art using routine experimentation.

In another embodiment, the treatment can result in cell-cycle inhibition of tumor cells (i.e., cytostasis). In another embodiment, the treatment can result in a T-cell mediated killing of the tumor cells.

As used herein, the terms "effective amount" and "therapeutically effective amount" refer to the quantity of active therapeutic agent or agents sufficient to yield a desired therapeutic response without undue adverse side effects such as toxicity, irritation, or allergic response. The specific "effective amount" will, obviously, vary with such factors as the particular condition being treated, the physical condition of the subject, the type of animal being treated, the duration of the treatment, the nature of concurrent therapy (if any), and the specific formulations employed and the structure of the compounds or its derivatives.

In some embodiments, the bispecific antibody of the present invention is used for treatment in addition to standard treatment options, for example surgery and radiation therapy. In some embodiments, the antibodies of the present disclosure are used in combination therapy, e.g. therapy including one or more different anti-cancer agents.

Suitable CD30+ cancers include, hematologic malignancies, for example, Hodgkins lymphoma, anaplastic large cell lymphoma, acute myeloid leukemia (AML), ovarian cancer, mesothelioma, skin squamous cell carcinoma, triple negative breast cancer, pancreatic cancer, small cell lung cancer, anal cancer, and thyroid carcinoma, among others. CD30 has also been shown to be expressed on a subset of non-Hodgkin's lymphomas (NHL), including Burkitt's lymphoma, anaplastic large-cell lymphomas (ALCL), cutaneous T-cell lymphomas, nodular small cleaved-cell lymphomas, lymphocytic lymphomas, peripheral T-cell lymphomas, Lennert's lymphomas, immunoblastic lymphomas, T-cell leukemia/lymphomas (ATLL), adult T-cell leukemia (T-ALL), and entroblastic/centrocytic (cb/cc) follicular lymphomas, along with embryonal carcinomas, nonembryonal carcinomas, malignant melanomas, and mesenchymal tumors. As such, the present methods may be used to treat any cancer in which CD30+ tumor cells are found.

As used herein, the terms "administering" and "administration" refer to any method of providing a pharmaceutical preparation to a subject. Such methods are well known to those skilled in the art and include, but are not limited to, oral administration, transdermal administration, administration by inhalation, nasal administration, topical administration, intravaginal administration, intraaural administration, rectal administration, sublingual administration, buccal administration, and parenteral administration, including injectable such as intravenous administration, intra-arterial administration, intramuscular administration, intradermal administration, intrathecal administration and subcutaneous administration. Administration can be continuous or intermittent. In various aspects, a preparation can be administered therapeutically; that is, administered to treat an existing disease or condition. In a preferred embodiment, the administration is intravenous administration.

The present invention also includes anti-CD3/anti-CD30 bispecific antibodies which exhibit one or more characteristics selected from the group consisting of: (a) inducing T cell proliferation; (b) activating T-cells, inducing IFN-gamma release; (c) inducing T-cell mediated cytotoxicity on anti-CD30+ tumor cells; (d) increasing CD30+ tumor cell death; and (e) decreasing CD30+ tumor volume.

Kits

In some embodiments, kits for carrying out the methods described herein are provided. The kits provided may contain the necessary components with which to carry out one or more of the above-noted methods. In one embodiment, kits for treating a subject with a CD30 cancer are provided. The kit comprises a bispecific antibody described herein and instructions for use. Further, the kit may comprise a pharmaceutically acceptable carrier and instructions for use.

The present invention has been described in terms of one or more preferred embodiments, and it should be appreciated that many equivalents, alternatives, variations, and modifications, aside from those expressly stated, are possible and within the scope of the invention.

It should be apparent to those skilled in the art that many additional modifications beside those already described are possible without departing from the inventive concepts. In interpreting this disclosure, all terms should be interpreted in the broadest possible manner consistent with the context. Variations of the term "comprising" should be interpreted as referring to elements, components, or steps in a non-exclusive manner, so the referenced elements, components, or steps may be combined with other elements, components, or steps that are not expressly referenced. Embodiments referenced as "comprising" certain elements are also contemplated as "consisting essentially of" and "consisting of" those elements. The term "consisting essentially of" and "consisting of" should be interpreted in line with the MPEP and relevant Federal Circuit interpretation. The transitional phrase "consisting essentially of" limits the scope of a claim to the specified materials or steps "and those that do not materially affect the basic and novel characteristic(s)" of the claimed invention. "Consisting of" is a closed term that excludes any element, step or ingredient not specified in the claim. For example, with regard to sequences "consisting of" refers to the sequence listed in the SEQ ID NO. and does refer to larger sequences that may contain the SEQ ID as a portion thereof.

The invention will be more fully understood upon consideration of the following non-limiting examples.

The present invention has been described in terms of one or more preferred embodiments, and it should be appreciated that many equivalents, alternatives, variations, and modifications, aside from those expressly stated, are possible and within the scope of the invention.

The invention will be more fully understood upon consideration of the following non-limiting examples.

EXAMPLES

Example 1: Anti-CD30 Monoclonal Antibody Production

Figure 2:
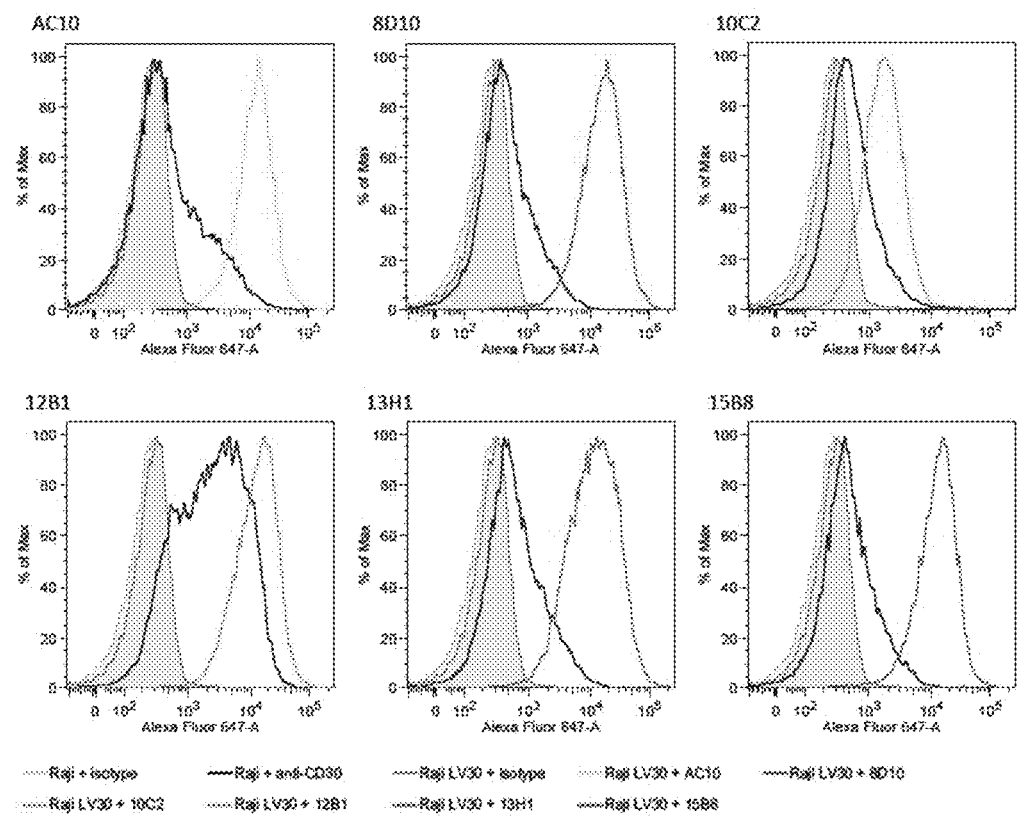
FIG. 2 depicts specific binding of the CD30 antibodies using flow cytometry on non-transduced Raji (low levels of endogenous CD30 expression) and LV transduced CD30+ Raji cells (high levels of CD30 expression).

We have employed hybridoma technology to generate novel murine anti-human CD30 mAbs. Mice were immunized and boosted with purified human GST-tagged CD30. Mouse spleen cells were then harvested and fused with myeloma cells to generate antibody secreting hybridoma. Hybridoma supernatants were screened for specificity to purified CD30 protein by ELISA, and GST specific clones were eliminated. Fifteen anti-human CD30 hybridoma cell lines were made, five were selected for further analysis. Specific binding of our mAbs to cell-surface expressed CD30 was assessed by flow cytometry (FIG. 1A-C) using 293T cells (CD30−), lentiviral transduced 293T cells expressing huCD30, and K562 cells which are naturally CD30+. The 293T (CD30−), 293T LV huCD30 (transduced with human CD30), SU-DHL-1 (lymphoma), RPMI.6666 (lymphoma) or K562 (CML) cell lines were incubated with each antibody in the form of unpurified hybridoma supernatant, and then incubated with an Alexa Fluor 647-labeled anti-mouse IgG antibody. Cell-associated fluorescence was determined by FACS. FIG. 2 demonstrates binding of purified antibodies to cells with CD30 surface expression.

Each of five hybridoma clones, designated as 8D10, 10C2, 12B1, 13H1, and 15B8, bound to CD30+ but not CD30− cell lines indicating specificity for the selected antigen. See FIG. 1 and FIG. 2.

All candidates show specific binding to CD30 and have been DNA and protein sequenced. The percentage identity between the heavy and light chains of the monoclonal antibodies selected were compared with the results shown in FIG. 3A and FIG. 3B.

CD30 mAb Binding—ELISA

Figure 4:
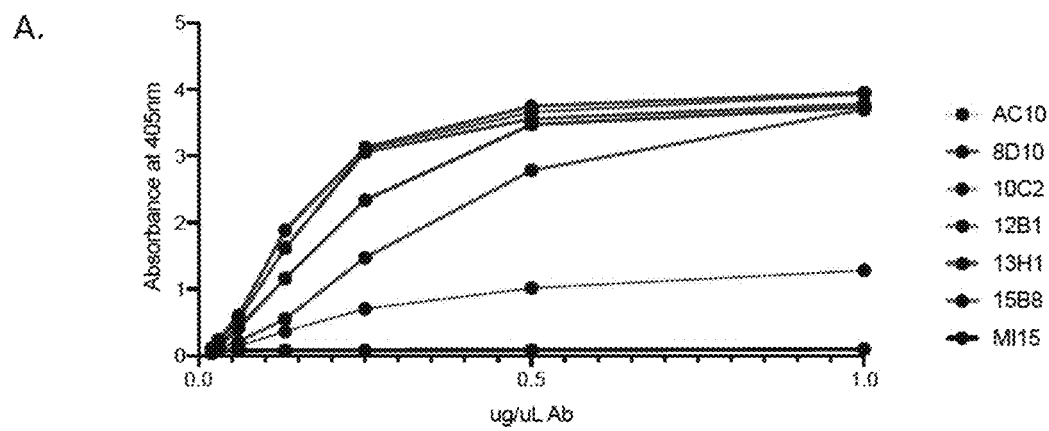
FIG. 4 depicts the binding of the antibodies to CD30 as measured by ELISA.
Figure 5:
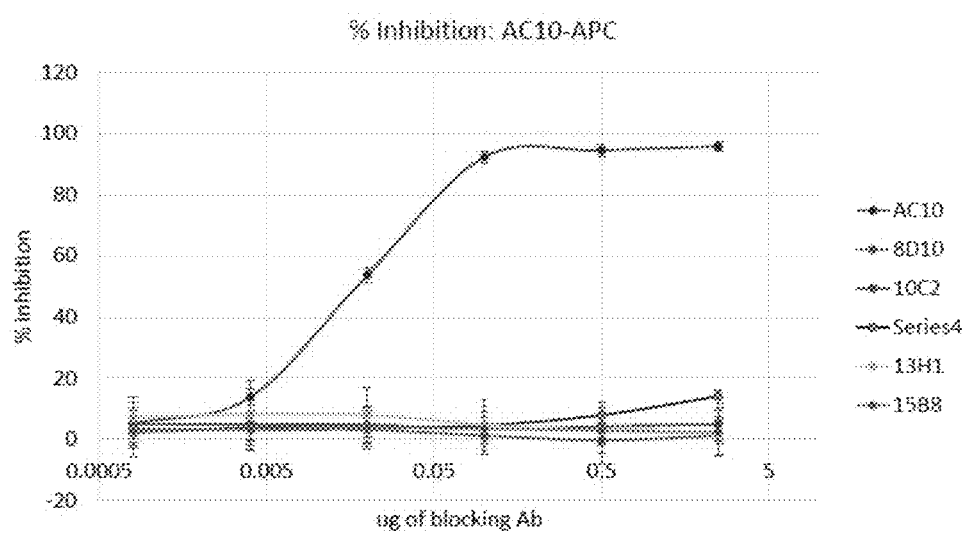
FIG. 5 depicts the percent inhibition of AC10 binding to CD30$^+$ cells (SU-DHL-1 cells) by 8D10, 10C2, 12B1, 13H1, 15B8, or AC10 antibodies.
Figure 6:
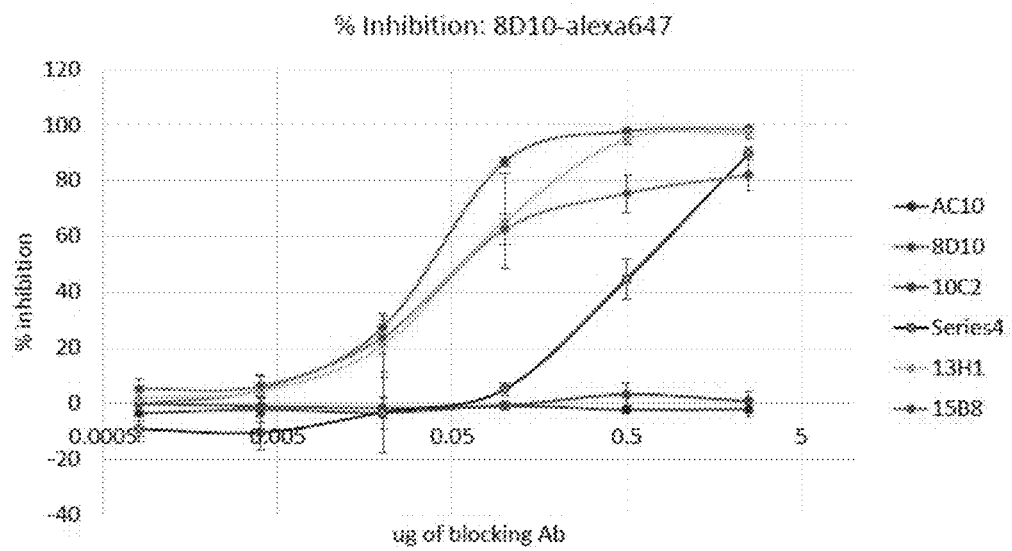
FIG. 6 depicts the percent inhibition of 8D10 binding to CD30$^+$ cells (SU-DHL-1 cells) by 8D10, 10C2, 12B1, 13H1, 15B8, or AC10 antibodies.
Figure 7:
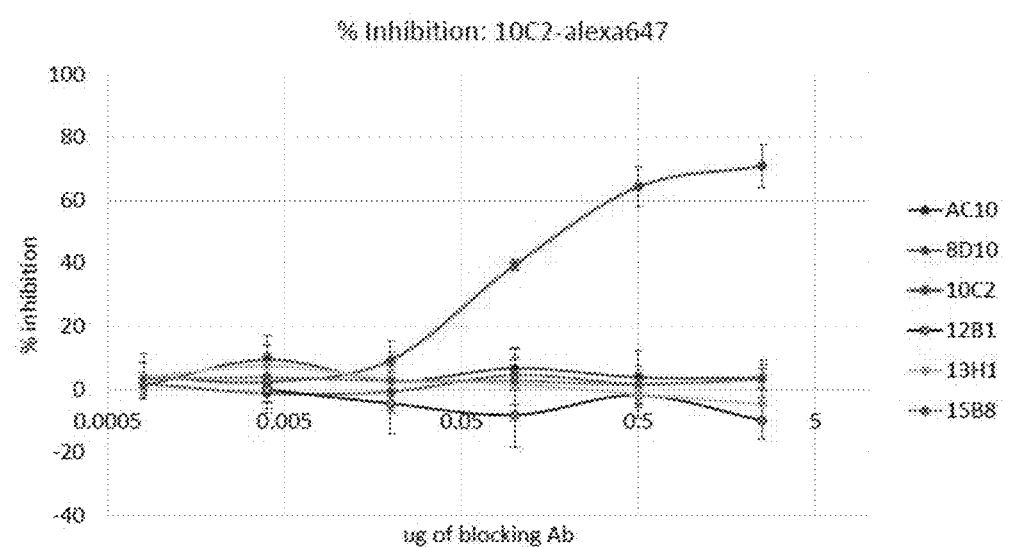
FIG. 7 depicts the percent inhibition of 10C2 binding to CD30$^+$ cells (SU-DHL-1 cells) by 8D10, 10C2, 12B1, 13H1, 15B8, or AC10 antibodies.
Figure 8:
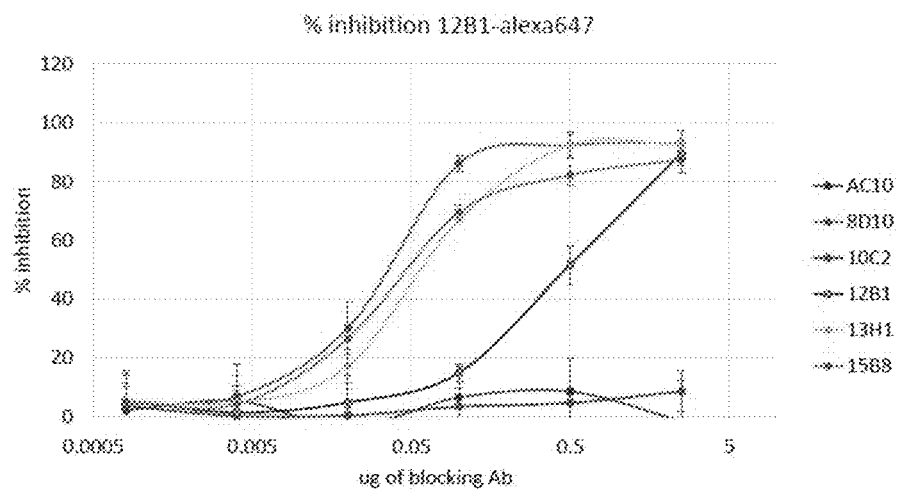
FIG. 8 depicts the percent inhibition of 12B1 binding to CD30$^+$ cells (SU-DHL-1 cells) by 8D10, 10C2, 12B1, 13H1, 15B8, or AC10 antibodies.
Figure 9:
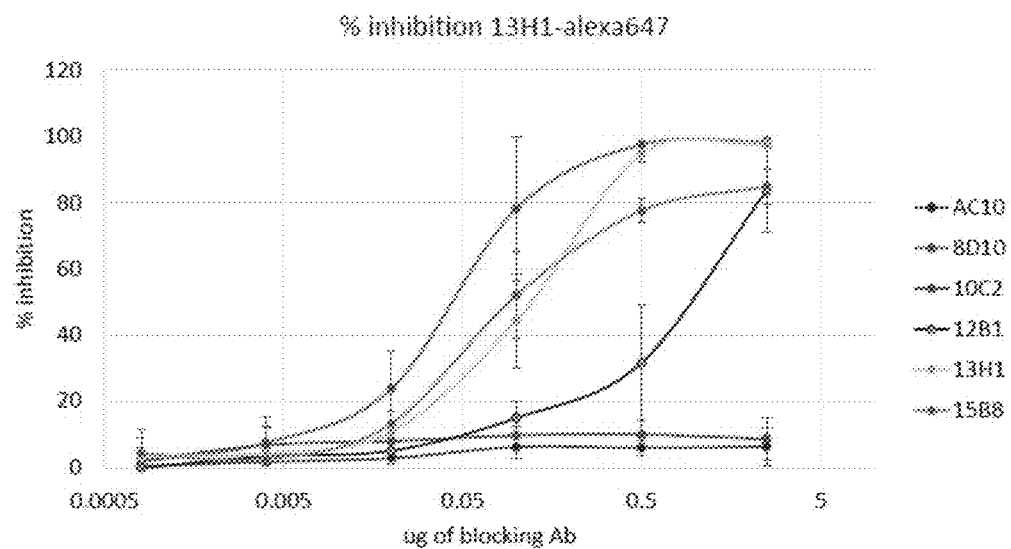
FIG. 9 depicts the percent inhibition of 13H1 binding to CD30$^+$ cells (SU-DHL-1 cells) by 8D10, 10C2, 12B1, 13H1, 15B8, or AC10 antibodies.
Figure 10:
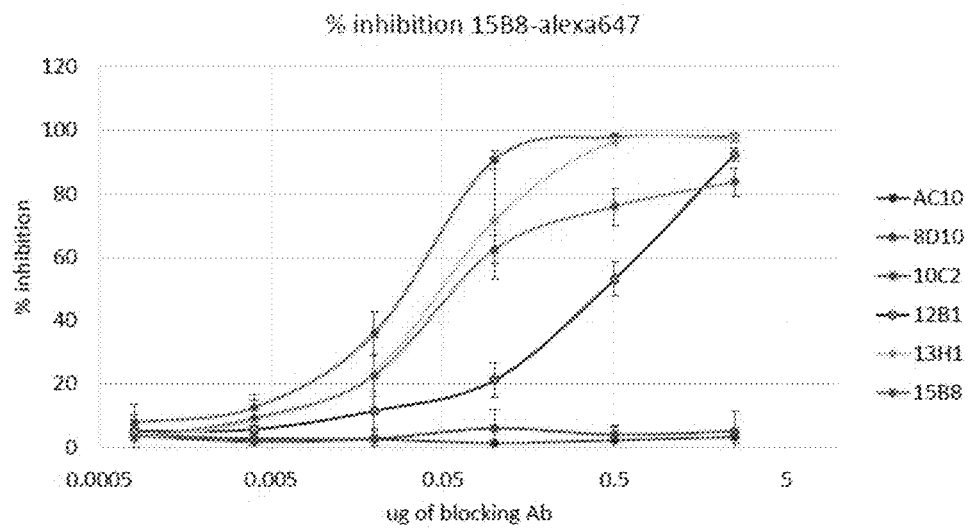
FIG. 10 depicts the percent inhibition of 15B8 binding to CD30$^+$ cells (SU-DHL-1 cells) by 8D10, 10C2, 12B1, 13H1, 15B8, or AC10 antibodies.

Microtiter plates were coated with recombinant CD30-GST fusion protein. Wells were blocked with 5% bovine serum albumin (BSA) solution. Purified 8D10, 10C2, 12B1, 13H1, 15B8, BY88 (commercial anti-CD30 antibody), AC10 (commercial anti-CD30 antibody) or MI15 (commercial anti-CD138 antibody) were added and incubated at varying concentrations. Wells were detected by incubating with an alkaline phosphatase-labeled anti-mouse IgG antibody. The plate was developed with pNPP (p-nitrophenyl phosphate). The optical density at 405 was determined using a plate reader and the results are shown in FIG. 4.

CD30 Mab Epitope Studies.

Figure 11:
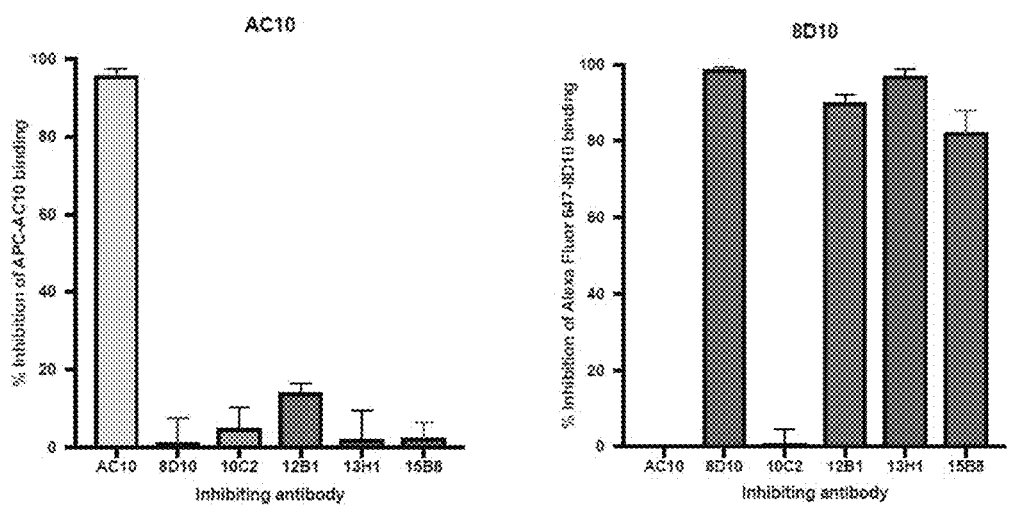
FIG. 11 is a set of bar graphs summarizing the blocking ability of the antibodies to AC10 (left) and 8D10 (right) binding to CD30$^+$ cells.
Figure 12:
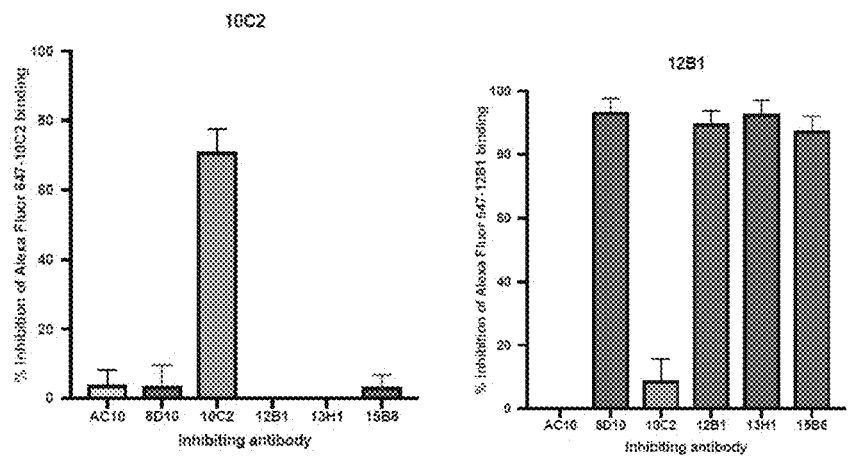
FIG. 12 is a set of bar graphs summarizing the blocking ability of the antibodies to 10C2 (left) and 12B1 (right) binding to CD30$^+$ cells.
Figure 13:
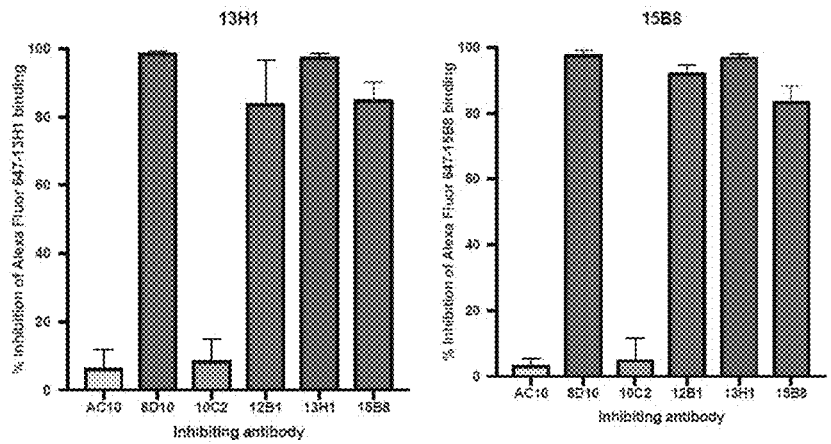
FIG. 13 is a set of bar graphs summarizing the blocking ability of the antibodies to 13H1 (left) and 15B8 (right) binding to CD30$^+$ cells.

CD30+SU-DHL-1 cells were blocked with unlabeled 8D10, 10C2, 12B1, 13H1, 15B8, or AC10 at 6 serial dilutions. The blocked cells were then incubated with fluorescently-labeled 8D10, 10C2, 12B1, 13H1, 15B8, or AC10. Excess labelled antibody was washed from the cells, and the cell-associated fluorescence was determined by FACS. Data is shown as a curve, plotted against increasing concentrations of blocking ab (FIGS. 5-10), and as a bar graph showing that values at the maximum concentration (2.5 ug) of blocking antibody (FIGS. 11-13).

All five antibodies have unique light and heavy chain sequences. These sequences also differ from the FDA-approved anti-CD30 antibody AC10 (Brentuximab vedotin). All five antibodies bind to CD30, as indicated by FACS and ELISA assays. All five antibodies bind to an epitope that is different from AC10 (Brentuximab). 8D0, 12B1, 13H1, 15B8 bind to the same or similar epitope as each other while 10C2 binds to an epitope that is distinct both from AC10, and from the other four novel antibodies reported here. FIGS. 19A-19B demonstrates the binding specificity of the new CD30 antibodies.

All antibodies bind an epitope distinct from Brentuximab vedotin.

Example 2: Bispecific CD30-CD3 Antibody as Immunotherapy for Hodgkin Lymphoma

This Example demonstrates the ability to make bispecific antibodies that bind to CD30 and to T cells (via CD3) to produce an anti-cancer effect for Hodgkin's Lymphoma. Two anti-CD30 clones (8D10 and 10C2) were covalently heteroconjugated to an anti-T cell antibody (CD3) (OKT3).

FACS was used to demonstrates that the hetero-conjugated CD30 antibodies bind to both a CD30+ Hodgkin's Lymphoma cell line (SU-DHL-1 cells, FIG. 14B) and to primary human T cells (FIG. 14B) for both the 8D10biAb (red) and 10C2 biAb (blue).

Figure 17A:
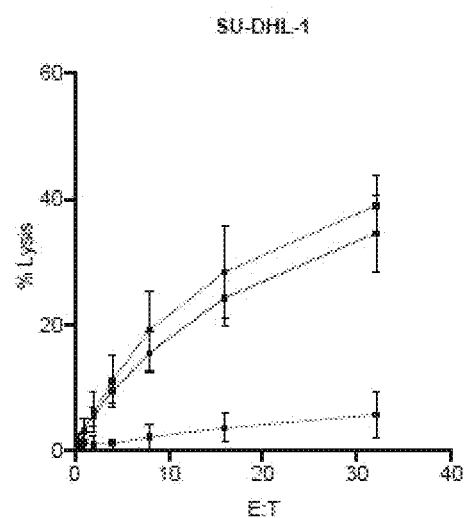
FIGS. 17A-17D demonstrate cytotoxicity of the biAbs of the present invention. Chromium release assay demonstrating the cytotoxicity of 8D10 and 10C2 biAb-armed T cells against CD30+ tumor cells. CD30+ tumor cell lines SU-DHL-1 (FIG. 17A), RPMI6666 (FIG. 17B) and Raji LV30 (FIG. 17D, Raji cells transduced with CD30 lentivirus) are killed with varying efficacy by 8D10 and 10C2 biAb-armed T cells. Non-transduced Raji cells (FIG. 17C, CD30–) are not killed by the armed T cells. Activated T cells may express low levels of CD30, which could be detrimental to the success of this biAb therapy.
Figure 17B:
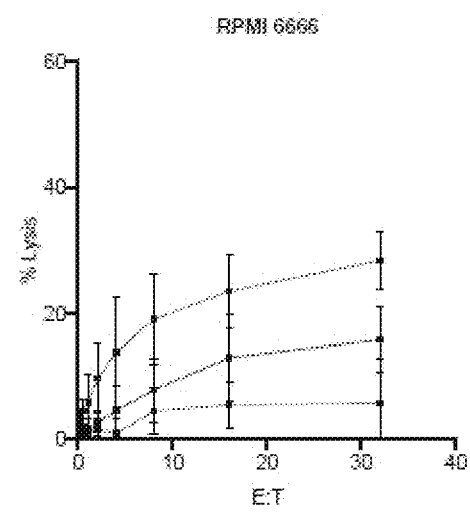
Figure 17C:
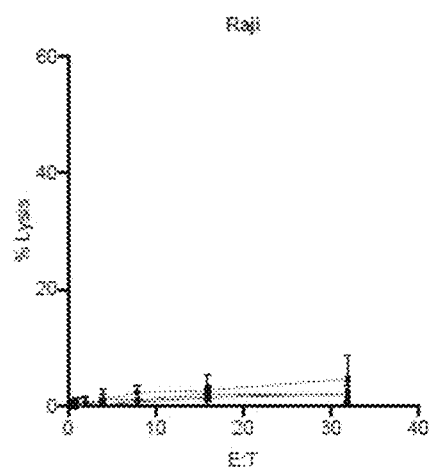
Figure 17D:
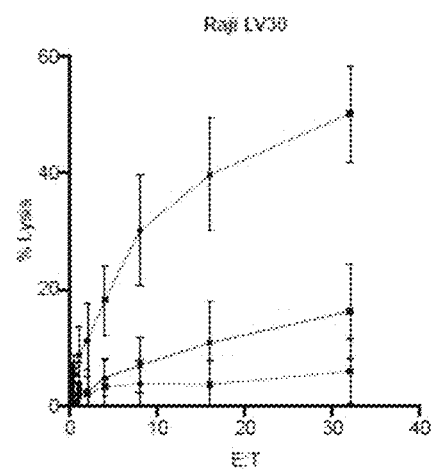

The ability of the biAb to bind T cells was also confirmed using fluorescently labelled T cells and labelled CD30+ tumor cells by measuring the formation of T cell-tumor cell dual-color conjugates, which only in the presence of biAb (FIG. 14E top right corner). The ability of the biAb to conjugate T cells and tumor cells was quantitated as shown in FIG. 17D.

The ability to stimulate the effector function of T cells was measured by production of pro-inflammatory cytokines IFN-γ and IL-2. As shown in FIGS. 16A-18B, 8D10 biAb or 10C2 biAb-armed T cells produce the pro-inflammatory cytokines IFN-γ (A) and IL-2 (B) when co-cultured with CD30+ tumor cells, indicating that binding of T cells to the biAb is sufficient to trigger T cell activation and cytotoxicity. Armed T cells cocultured with CD30− cells have much lower cytokine production demonstrating the specificity of this approach. The cytotoxicity of the biAbs was also confirmed by cell death in the presence of the 8D10 and 10C2 biAb-armed T cells against CD30+ tumor cells. CD30+ tumor cell lines SU-DHL-1, RPMI6666 and Raji LV30 (Raji cells transduced with CD30 lentivirus) are killed with varying efficacy by 8D10 and 10C2 biAb-armed T cells as demonstrated in FIGS. 17A-17D. Non-transduced Raji cells (FIG. 18A, CD30−) are not killed by the armed T cells. FIG. 18B demonstrates that the CD30 expression on activated T cells is low enough to avoid elimination by the 8D10 and 10C2 biAb armed T cells.

As such, this Example demonstrates the ability and specificity of the biAb to activate T cells and kill tumor cells. The bispecific antibody results in the release of proinflammatory cytokines, which triggers T cell cytotoxicity specifically against CD30+ cells, while sparring CD30− cells. Also, T cell fratricide as a result of low CD30 expression on activated T cells is not observed.

Each publication, patent, and patent publication cited in this disclosure is incorporated in reference herein in its entirety. The present invention is not intended to be limited to the foregoing examples, but encompasses all such modifications and variations as come within the scope of the appended claims.

REFERENCE TO A SEQUENCE LISTING SUBMITTED VIA EFS-WEB

The content of the ASCII text file of the sequence listing named "650053.00647_ST25.txt" which is 16.5 kb in size Anti-CD30 mAb CDR
8D10-Light chain
(SEQ ID NO: 1)
DIVMTQSPASQSASLGESVTITC<u>LASQTIGTWLA</u>WYQQKPGKSPQFLIYA

ATSLADGVPSRF SGSGSGTKFSFKISSLQAEDFVSYYC<u>QQLYSTPFT</u>FG

GGTKLEIK (CDRL1-SEQ ID NO: 2-underline; CDRL2-SEQ ID NO: 3-bold; CDRL3-SEQ ID NO: 4-bold/underline)

8D10-Heavy chain
(SEQ ID NO: 5)
QVQLQESGTELVKPGASVKLSCKAS<u>GYTFTSY</u>WMHWMKQRPGQGLEWIGN

INPSNGGTNYNEKFKNKATLTVDKSSSTAYMQLSSLTSEDSAVYYCARR<u>D</u>

<u>YYYGSSYGFDV</u>WGTGTTVTVSS (CDH1-SEQ ID NO: 6-underline; CDH2-SEQ ID NO: 7-bold; CDH3-SEQ ID NO: 8-bold/underline)

10C2-Light chain
(SEQ ID NO: 9)
DIVLTQTPLTLSVTIGQPASISC<u>KSNQSLLDSYGKTYLN</u>WLLQRPGQSPK RLIYLVSKLDSGVPDRFTGSGSGTDFTLKISRVEAEDLGVYYC<u>WQGTHFP</u>

<u>RT</u>FGGGTKLEIK (CDRL1-SEQ ID NO: 10-underline; CDRL2-SEQ ID NO: 11-bold; CDRL3-SEQ ID NO: 12-bold/underline)

10C2-Heavy chain
(SEQ ID NO: 13)
QVQLEQSGPVLVKPGASVKMSCKAS<u>GYTFTDY</u>YMNWVKQSHGKSLEWIGV

INPYNGGTSYNQKFKGKATLTVDKSSSTACMELNCLTSEDSAVYYCTL<u>GA</u>

<u>Y</u>VVGQGTSVTVSS (CDH1-SEQ ID NO: 14-underline; CDH2-SEQ ID NO: 15-bold; CDH3-SEQ ID NO: 16-bold/underline)

12B1-Light chain
(SEQ ID NO: 17)
DIVMTQTTASLSTSVGETVTITC<u>RASGNLHSYLT</u>WYQQKQGKSPQLLVYN

AKTLADGVPSRFSGSGSGTQYSLKIDSLQPEDFGSYYC<u>QHFWTTPFT</u>FGS

GTKLEIK (CDRL1-SEQ ID NO: 18-underline; CDRL2-SEQ ID NO: 19-bold; CDRL3-SEQ ID NO: 20-bold/underline)

12B-1Heavy chain
(SEQ ID NO: 21)
EVKLEESGTELVKPGASVKLSCKAS<u>GYTFTSY</u>WMHWVKQRPGQGLEWIGN

INPTNGGTNYNEKFKSKATLTVDKSSRTAYMQLSSLTSGDSAVYYCARR<u>D</u>

<u>FITTSGFAY</u>WGQGTLVTVSA (CDH1-SEQ ID NO: 22-underline; CDH2-SEQ ID NO: 23-bold; CDH3-SEQ ID NO: 24-bold/underline)

13H1 Light chain
(SEQ ID NO: 25)
DIVMTQTPKSMSMSVGERVTLSC<u>KASENVGTYVS</u>WYQQKPEQSPKVLIYG

ASNRFTGVPDRFTGSGSATDFTLTISSVQTEDLADYHC<u>GQSYSYPLT</u>FGA

GTKLELK (CDRL1-SEQ ID NO: 26-underline; CDRL2-SEQ ID NO: 27-bold; CDRL3-SEQ ID NO: 28-bold/underline)

13H1-Heavy chain
(SEQ ID NO: 29)
QVQLQQSGTELVKPGASVKLSCKAS<u>GHTFTSY</u>WMHWVKQRPGQGLEWIGN

INPSNGGTNYNEKFKSKATLTVDKSSSTAYMQLSSLTSEDSAVYYCARR<u>G</u>

<u>YYGSSSYWSFDV</u>WGTGTTVTVSS (CDH1-SEQ ID NO: 30-underline; CDH2-SEQ ID NO: 31-bold; CDH3-SEQ ID NO: 32-bold/underline)

15B8 Light chain
(SEQ ID NO: 33)
DIVMTQTPASLSASVGETVTITC<u>RASGNIHNYLA</u>WYQQKQGKSPQLLVYN

AKTLADGVPSRF SGSGSGTQYSLKINSLQPEDFGSYYC<u>QHFWSTPFT</u>F

GSGTKLEIK (CDRL1-SEQ ID NO: 34-underline; CDRL2-SEQ ID NO: 35-bold; CDRL3-SEQ ID NO: 36-bold/underline)

15B8-Heavy chain
(SEQ ID NO: 37)
QVQLEQSGTELVKPGASVKLSCKAS<u>GYTFTSY</u>WMHWVKQRPGQGLEWIGN

INPSNGGTNYNEKFKSKATLTVDKSSSTAYMQLSSLTSEDSAIYYCARR<u>N</u>

<u>NYYASSPFAY</u>WGQGTLVSVSA (CDH1-SEQ ID NO: 38-underline; CDH2-SEQ ID NO: 39-bold; CDH3-SEQ ID NO: 40-bold/underline was created on Sep. 24, 2019 and electronically submitted via EFS-Web herewith the application is incorporated herein by reference in its entirety.

The invention claimed is:

1. An isolated bispecific antibody capable of binding human CD30 and to CD3 comprising an anti-CD30 antibody or antigen binding portion thereof and an anti-CD3 antibody or antigen binding portion thereof, wherein the anti-CD30 antibody or antigen binding portion thereof comprises:

(a) a light chain variable domain comprising a CDRL1 region of SEQ ID NO:2 or a sequence with at least 85% similarity to SEQ ID NO:2, a CDRL2 region of SEQ ID NO:3 or a sequence with at least 85% similarity to SEQ ID NO:3, and a CDRL3 region of SEQ ID NO:4 or a sequence with at least 85% similarity to SEQ ID NO:4 and a heavy chain variable domain comprising a CDRH1 region of SEQ ID NO:6 or a sequence with at least 85% similarity to SEQ ID NO:6, a CDRH2 region of SEQ ID NO:7 or a sequence with at least 85% similarity to SEQ ID NO:7, and a CDRH3 region of SEQ ID NO:8 or a sequence with at least 85% similarity to SEQ ID NO:8;

(b) a light chain variable domain comprising a CDRL1 region of SEQ ID NO:10 or a sequence with at least 85% similarity to SEQ ID NO:10, a CDRL2 region of SEQ ID NO:11 or a sequence with at least 85% similarity to SEQ ID NO:11, and a CDRL3 region of SEQ ID NO:12 or a sequence with at least 85% similarity to SEQ ID NO:12 and a heavy chain variable domain comprising a CDRH1 region of SEQ ID NO:14 or a sequence with at least 85% similarity to SEQ ID NO:14, a CDRH2 region of SEQ ID NO:15 or a sequence with at least 85% similarity to SEQ ID NO:15, and a CDRH3 region of SEQ ID NO:16 or a sequence with at least 85% similarity to SEQ ID NO:16;
(c) a light chain variable domain comprising a CDRL1 region of SEQ ID NO:18 or a sequence with at least 85% similarity to SEQ ID NO:18, a CDRL2 region of SEQ ID NO:19 or a sequence with at least 85% similarity to SEQ ID NO:19, and a CDRL3 region of SEQ ID NO:20 or a sequence with at least 85% similarity to SEQ ID NO:20 and a heavy chain variable domain comprising a CDRH1 region of SEQ ID NO:22 or a sequence with at least 85% similarity to SEQ ID NO:22, a CDRH2 region of SEQ ID NO:23 or a sequence with at least 85% similarity to SEQ ID NO:23, and a CDRH3 region of SEQ ID NO:24 or a sequence with at least 85% similarity to SEQ ID NO:24;
(d) a light chain variable domain comprising a CDRL1 region of SEQ ID NO:26 or a sequence with at least 85% similarity to SEQ ID NO:26, a CDRL2 region of SEQ ID NO:27 or a sequence with at least 85% similarity to SEQ ID NO:27, and a CDRL3 region of SEQ ID NO:28 or a sequence with at least 85% similarity to SEQ ID NO:28 and a heavy chain variable domain comprising a CDRH1 region of SEQ ID NO:30 or a sequence with at least 85% similarity to SEQ ID NO:30, a CDRH2 region of SEQ ID NO:31 or a sequence with at least 85% similarity to SEQ ID NO:31, and a CDRH3 region of SEQ ID NO:32 or a sequence with at least 85% similarity to SEQ ID NO:32; or
(e) a light chain variable domain comprising a CDRL1 region of SEQ ID NO:34 or a sequence with at least 85% similarity to SEQ ID NO:34, a CDRL2 region of SEQ ID NO:35 or a sequence with at least 85% similarity to SEQ ID NO:35, and a CDRL3 region of SEQ ID NO:36 or a sequence with at least 85% similarity to SEQ ID NO:36 and a heavy chain variable domain comprising a CDRH1 region of SEQ ID NO:38 or a sequence with at least 85% similarity to SEQ ID NO:38, a CDRH2 region of SEQ ID NO:39 or a sequence with at least 85% similarity to SEQ ID NO:39, and a CDRH3 region of SEQ ID NO:40 or a sequence with at least 85% similarity to SEQ ID NO:40.

2. The isolated bispecific antibody of claim 1, wherein the anti-CD30 antibody or antigen binding portion thereof comprises a heavy and a light chain selected from the group consisting of:
(a) a light chain comprising SEQ ID NO:1 or a sequence with at least 85% similarity to SEQ ID NO:1, and a heavy chain comprising SEQ ID NO:5 or a sequence with at least 85% similarity to SEQ ID NO:5;
(b) a light chain comprising SEQ ID NO:9 or a sequence with at least 85% similarity to SEQ ID NO:9, and a heavy chain comprising SEQ ID NO:13 or a sequence with at least 85% similarity to SEQ ID NO:13;
(c) a light chain comprising SEQ ID NO:17 or a sequence with at least 85% similarity to SEQ ID NO:17, and a heavy chain comprising SEQ ID NO:21 or a sequence with at least 85% similarity to SEQ ID NO:21;
(d) a light chain comprising SEQ ID NO:25 or a sequence with at least 85% similarity to SEQ ID NO:25, and a heavy chain comprising SEQ ID NO:29 or a sequence with at least 85% similarity to SEQ ID NO:29; and
(e) a light chain comprising SEQ ID NO:33 or a sequence with at least 85% similarity to SEQ ID NO:33, and a heavy chain comprising SEQ ID NO:37 or a sequence with at least 85% similarity to SEQ ID NO:37.

3. The isolated bispecific antibody of claim 1, wherein the anti-CD30 antibody or antigen binding portion thereof is directly or indirectly conjugated to the T cell surface antigen antibody or antigen binding portion thereof.

4. The isolated bispecific antibody of claim 3, wherein the anti-CD30 antibody or antigen binding portion thereof is directly conjugated to the T cell surface antigen antibody or antigen binding portion thereof.

5. The isolated bispecific antibody of claim 4, wherein the anti-CD30 antibody or antigen binding portion thereof is directly conjugated to the T cell surface antigen antibody or antigen binding portion thereof via a linker.

6. The isolated bispecific antibody of claim 1, wherein the anti-CD3 antibody is a monoclonal antibody.

7. The isolated bispecific antibody of claim 6, wherein the anti-CD3 antibody is OKT3 made by the hybridoma with ATCC accession number CRL 8001.

8. A pharmaceutical composition comprising the isolated bispecific antibody of claim 1 and a pharmaceutically acceptable carrier.

9. A method of treating a patient having a CD30+ cancer, the method comprising
(a) administering a therapeutically effective amount of the bispecific antibody of claim 1 to reduce or inhibit CD30+ cancer growth.

10. The method of claim 9, wherein the CD30+ cancer is Hodgkin's lymphoma or AML.

11. The method of claim 9, wherein the method further comprises administering an effective amount of a cancer treatment.

12. A method of inhibiting growth of a tumor cell expressing CD30, comprising contacting the tumor cell with an effective amount of the antibody or antigen binding fragment thereof of claim 1 such that the growth of the cell is inhibited.

13. A method of enhancing a T cell-mediated immune response against a CD30+ tumor cell, the method comprising administering a therapeutically effective amount of the bispecific antibody of claim 1 to increase the T cell-mediated immune response as compared to treatment without the bispecific antibody.

14. An isolated bispecific antibody capable of binding human CD30 and to a NK cell surface antigen, the bispecific antibody comprising an anti-CD30 antibody or antigen binding portion thereof and an anti-NK cell surface antigen antibody or antigen binding portion thereof,
wherein the anti-NK cell surface antigen antibody or antigen binding portion thereof is an anti-CD16 antibody, and
wherein the anti-CD30 antibody or antigen binding portion thereof comprises:
(a) a light chain variable domain comprising a CDRL1 region of SEQ ID NO:2, a CDRL2 region of SEQ ID NO:3, and a CDRL3 region of SEQ ID NO:4 and a heavy chain variable domain comprising a CDRH1 region of SEQ ID NO:6, a CDRH2 region of SEQ ID NO:7, and a CDRH3 region of SEQ ID NO:8;
(b) a light chain variable domain comprising a CDRL1 region of SEQ ID NO:10, a CDRL2 region of SEQ ID NO:11, and a CDRL3 region of SEQ ID NO:12 and a heavy chain variable domain comprising a CDRH1 region of SEQ ID NO:14, a CDRH2 region of SEQ ID NO:15, and a CDRH3 region of SEQ ID NO:16;
(c) a light chain variable domain comprising a CDRL1 region of SEQ ID NO:18, a CDRL2 region of SEQ ID NO:19, and a CDRL3 region of SEQ ID NO:20 and a heavy chain variable domain comprising a CDRH1 region of SEQ ID NO:22, a CDRH2 region of SEQ ID NO:23, and a CDRH3 region of SEQ ID NO:24;

(d) a light chain variable domain comprising a CDRL1 region of SEQ ID NO:26, a CDRL2 region of SEQ ID NO:27, and a CDRL3 region of SEQ ID NO:28 and a heavy chain variable domain comprising a CDRH1 region of SEQ ID NO:30, a CDRH2 region of SEQ ID NO:31, and a CDRH3 region of SEQ ID NO:32; or (e) a light chain variable domain comprising a CDRL1 region of SEQ ID NO:34, a CDRL2 region of SEQ ID NO:35, and a CDRL3 region of SEQ ID NO:36 and a heavy chain variable domain comprising a CDRH1 region of SEQ ID NO:38, a CDRH2 region of SEQ ID NO:39, and a CDRH3 region of SEQ ID NO:40.

15. The isolated bispecific antibody of claim 14, wherein the anti-CD30 antibody or antigen binding portion thereof comprises a heavy and a light chain selected from the group consisting of:

(a) a light chain comprising SEQ ID NO:1 or a sequence with at least 85% similarity to SEQ ID NO:1, and a heavy chain comprising SEQ ID NO:5 or a sequence with at least 85% similarity to SEQ ID NO:5;

(b) a light chain comprising SEQ ID NO:9 or a sequence with at least 85% similarity to SEQ ID NO:9, and a heavy chain comprising SEQ ID NO:13 or a sequence with at least 85% similarity to SEQ ID NO:13;

(c) a light chain comprising SEQ ID NO:17 or a sequence with at least 85% similarity to SEQ ID NO:17, and a heavy chain comprising SEQ ID NO:21 or a sequence with at least 85% similarity to SEQ ID NO:21;

(d) a light chain comprising SEQ ID NO:25 or a sequence with at least 85% similarity to SEQ ID NO:25, and a heavy chain comprising SEQ ID NO:29 or a sequence with at least 85% similarity to SEQ ID NO:29; and (e) a light chain comprising SEQ ID NO:33 or a sequence with at least 85% similarity to SEQ ID NO:33, and a heavy chain comprising SEQ ID NO:37 or a sequence with at least 85% similarity to SEQ ID NO:37.

16. An isolated bispecific antibody capable of binding human CD30 and to a surface receptor on T cells, the bispecific antibody comprising an anti-CD30 antibody or antigen binding portion thereof and an anti-CD3 antibody or antigen binding portion thereof, wherein the anti-CD30 antibody or antigen binding portion thereof comprises:

(a) a light chain variable domain comprising a CDRL1 region of SEQ ID NO:2 or a sequence with at least 85% similarity to SEQ ID NO:2, a CDRL2 region of SEQ ID NO:3 or a sequence with at least 85% similarity to SEQ ID NO:3, and a CDRL3 region of SEQ ID NO:4 or a sequence with at least 85% similarity to SEQ ID NO:4 and a heavy chain variable domain comprising a CDRH1 region of SEQ ID NO:6 or a sequence with at least 85% similarity to SEQ ID NO:6, a CDRH2 region of SEQ ID NO:7 or a sequence with at least 85% similarity to SEQ ID NO:7, and a CDRH3 region of SEQ ID NO:8 or a sequence with at least 85% similarity to SEQ ID NO:8;

(b) a light chain variable domain comprising a CDRL1 region of SEQ ID NO:10 or a sequence with at least 85% similarity to SEQ ID NO:10, a CDRL2 region of SEQ ID NO:11 or a sequence with at least 85% similarity to SEQ ID NO:11, and a CDRL3 region of SEQ ID NO:12 or a sequence with at least 85% similarity to SEQ ID NO:12 and a heavy chain variable domain comprising a CDRH1 region of SEQ ID NO:14 or a sequence with at least 85% similarity to SEQ ID NO:14, a CDRH2 region of SEQ ID NO:15 or a sequence with at least 85% similarity to SEQ ID NO:15, and a CDRH3 region of SEQ ID NO:16 or a sequence with at least 85% similarity to SEQ ID NO:16;

(c) a light chain variable domain comprising a CDRL1 region of SEQ ID NO:18 or a sequence with at least 85% similarity to SEQ ID NO:18, a CDRL2 region of SEQ ID NO:19 or a sequence with at least 85% similarity to SEQ ID NO:19, and a CDRL3 region of SEQ ID NO:20 or a sequence with at least 85% similarity to SEQ ID NO:20 and a heavy chain variable domain comprising a CDRH1 region of SEQ ID NO:22 or a sequence with at least 85% similarity to SEQ ID NO:22, a CDRH2 region of SEQ ID NO:23 or a sequence with at least 85% similarity to SEQ ID NO:23, and a CDRH3 region of SEQ ID NO:24 or a sequence with at least 85% similarity to SEQ ID NO:24;

(d) a light chain variable domain comprising a CDRL1 region of SEQ ID NO:26 or a sequence with at least 85% similarity to SEQ ID NO:26, a CDRL2 region of SEQ ID NO:27 or a sequence with at least 85% similarity to SEQ ID NO:27, and a CDRL3 region of SEQ ID NO:28 or a sequence with at least 85% similarity to SEQ ID NO:28 and a heavy chain variable domain comprising a CDRH1 region of SEQ ID NO:30 or a sequence with at least 85% similarity to SEQ ID NO:30, a CDRH2 region of SEQ ID NO:31 or a sequence with at least 85% similarity to SEQ ID NO:31, and a CDRH3 region of SEQ ID NO:32 or a sequence with at least 85% similarity to SEQ ID NO:32; or (e) a light chain variable domain comprising a CDRL1 region of SEQ ID NO:34 or a sequence with at least 85% similarity to SEQ ID NO:34, a CDRL2 region of SEQ ID NO:35 or a sequence with at least 85% similarity to SEQ ID NO:35, and a CDRL3 region of SEQ ID NO:36 or a sequence with at least 85% similarity to SEQ ID NO:36 and a heavy chain variable domain comprising a CDRH1 region of SEQ ID NO:38 or a sequence with at least 85% similarity to SEQ ID NO:38, a CDRH2 region of SEQ ID NO:39 or a sequence with at least 85% similarity to SEQ ID NO:39, and a CDRH3 region of SEQ ID NO:40 or a sequence with at least 85% similarity to SEQ ID NO:40.

17. A method of eliciting an immune response in a subject to a tumor antigen, the method comprising administering the bispecific antibody of claim 16 in an amount effective to elicit an immune response.

* * * * *

UNITED STATES PATENT AND TRADEMARK OFFICE
CERTIFICATE OF CORRECTION

| | |
|---|---|
| PATENT NO. | : 11,667,721 B2 |
| APPLICATION NO. | : 16/580625 |
| DATED | : June 6, 2023 |
| INVENTOR(S) | : Jeffrey A. Medin et al. |

It is certified that error appears in the above-identified patent and that said Letters Patent is hereby corrected as shown below:

In the Specification

Column 7, Line 20, "VH" should be --$V_H$--.

Column 7, Line 21, "(VL)" should be --($V_L$)--.

Column 7, Line 24, "VH" should be --$V_H$--.

Column 7, Line 25, "VL" should be --$V_L$--.

Column 13, Line 56, "VH and VL" should be --$V_H$ and $V_L$--.

Column 13, Line 57, "VH and VL" should be --$V_H$ and $V_L$--.

Column 16, Line 54, "primar" should be --primary--.

Column 17, Line 11, "(VH)" should be --($V_H$)--.

Column 17, Line 15, "(VL)" should be --($V_L$)--.

Signed and Sealed this
Fifteenth Day of August, 2023

Katherine Kelly Vidal
*Director of the United States Patent and Trademark Office*

SEQUENCE LISTING

```
<160> NUMBER OF SEQ ID NOS: 40

<210> SEQ ID NO 1
<211> LENGTH: 107
<212> TYPE: PRT
<213> ORGANISM: Artificial Sequence
<220> FEATURE:
<223> OTHER INFORMATION: synthetic - 8D10 light chain

<400> SEQUENCE: 1

Asp Ile Val Met Thr Gln Ser Pro Ala Ser Gln Ser Ala Ser Leu Gly
1               5                   10                  15

Glu Ser Val Thr Ile Thr Cys Leu Ala Ser Gln Thr Ile Gly Thr Trp
            20                  25                  30

Leu Ala Trp Tyr Gln Gln Lys Pro Gly Lys Ser Pro Gln Phe Leu Ile
        35                  40                  45

Tyr Ala Ala Thr Ser Leu Ala Asp Gly Val Pro Ser Arg Phe Ser Gly
    50                  55                  60
```

```
Ser Gly Ser Gly Thr Lys Phe Ser Phe Lys Ile Ser Ser Leu Gln Ala
65                  70                  75                  80

Glu Asp Phe Val Ser Tyr Tyr Cys Gln Gln Leu Tyr Ser Thr Pro Phe
                85                  90                  95

Thr Phe Gly Gly Gly Thr Lys Leu Glu Ile Lys
            100                 105
```

<210> SEQ ID NO 2
<211> LENGTH: 11
<212> TYPE: PRT
<213> ORGANISM: Artificial Sequence
<220> FEATURE:
<223> OTHER INFORMATION: synthetic - CDRL1

<400> SEQUENCE: 2

```
Leu Ala Ser Gln Thr Ile Gly Thr Trp Leu Ala
1               5                   10
```

<210> SEQ ID NO 3
<211> LENGTH: 7
<212> TYPE: PRT
<213> ORGANISM: Artificial Sequence
<220> FEATURE:
<223> OTHER INFORMATION: synthetic - CDRL2

<400> SEQUENCE: 3

```
Ala Ala Thr Ser Leu Ala Asp
1               5
```

<210> SEQ ID NO 4
<211> LENGTH: 9
<212> TYPE: PRT
<213> ORGANISM: Artificial Sequence
<220> FEATURE:
<223> OTHER INFORMATION: synthetic - CDRL3

<400> SEQUENCE: 4

```
Gln Gln Leu Tyr Ser Thr Pro Phe Thr
1               5
```

<210> SEQ ID NO 5
<211> LENGTH: 122
<212> TYPE: PRT
<213> ORGANISM: Artificial Sequence
<220> FEATURE:
<223> OTHER INFORMATION: synthetic - 8D10 heavy chain

<400> SEQUENCE: 5

```
Gln Val Gln Leu Gln Glu Ser Gly Thr Glu Leu Val Lys Pro Gly Ala
1               5                   10                  15

Ser Val Lys Leu Ser Cys Lys Ala Ser Gly Tyr Thr Phe Thr Ser Tyr
                20                  25                  30

Trp Met His Trp Met Lys Gln Arg Pro Gly Gln Gly Leu Glu Trp Ile
            35                  40                  45

Gly Asn Ile Asn Pro Ser Asn Gly Gly Thr Asn Tyr Asn Glu Lys Phe
    50                  55                  60

Lys Asn Lys Ala Thr Leu Thr Val Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Arg Asp Tyr Tyr Tyr Gly Ser Ser Tyr Gly Phe Asp Val Trp
                100                 105                 110
```

```
Gly Thr Gly Thr Thr Val Thr Val Ser Ser
        115                 120

<210> SEQ ID NO 6
<211> LENGTH: 7
<212> TYPE: PRT
<213> ORGANISM: Artificial Sequence
<220> FEATURE:
<223> OTHER INFORMATION: synthetic - CDH1

<400> SEQUENCE: 6

Gly Tyr Thr Phe Thr Ser Tyr
1               5

<210> SEQ ID NO 7
<211> LENGTH: 6
<212> TYPE: PRT
<213> ORGANISM: Artificial Sequence
<220> FEATURE:
<223> OTHER INFORMATION: synthetic - CDH2

<400> SEQUENCE: 7

Asn Pro Ser Asn Gly Gly
1               5

<210> SEQ ID NO 8
<211> LENGTH: 13
<212> TYPE: PRT
<213> ORGANISM: Artificial Sequence
<220> FEATURE:
<223> OTHER INFORMATION: synthetic - CDH3

<400> SEQUENCE: 8

Arg Asp Tyr Tyr Tyr Gly Ser Ser Tyr Gly Phe Asp Val
1               5                   10

<210> SEQ ID NO 9
<211> LENGTH: 112
<212> TYPE: PRT
<213> ORGANISM: Artificial Sequence
<220> FEATURE:
<223> OTHER INFORMATION: synthetic - 10C2 light chain

<400> SEQUENCE: 9

Asp Ile Val Leu Thr Gln Thr Pro Leu Thr Leu Ser Val Thr Ile Gly
1               5                   10                  15

Gln Pro Ala Ser Ile Ser Cys Lys Ser Asn Gln Ser Leu Leu Asp Ser
            20                  25                  30

Tyr Gly Lys Thr Tyr Leu Asn Trp Leu Leu Gln Arg Pro Gly Gln Ser
        35                  40                  45

Pro Lys Arg Leu Ile Tyr Leu Val Ser Lys Leu Asp Ser Gly Val Pro
    50                  55                  60

Asp Arg Phe Thr Gly Ser Gly Ser Gly Thr Asp Phe Thr Leu Lys Ile
65                  70                  75                  80

Ser Arg Val Glu Ala Glu Asp Leu Gly Val Tyr Tyr Cys Trp Gln Gly
                85                  90                  95

Thr His Phe Pro Arg Thr Phe Gly Gly Gly Thr Lys Leu Glu Ile Lys
            100                 105                 110

<210> SEQ ID NO 10
<211> LENGTH: 16
<212> TYPE: PRT
<213> ORGANISM: Artificial Sequence
```

```
<220> FEATURE:
<223> OTHER INFORMATION: synthetic - CDRL1

<400> SEQUENCE: 10

Lys Ser Asn Gln Ser Leu Leu Asp Ser Tyr Gly Lys Thr Tyr Leu Asn
1               5                   10                  15

<210> SEQ ID NO 11
<211> LENGTH: 7
<212> TYPE: PRT
<213> ORGANISM: Artificial Sequence
<220> FEATURE:
<223> OTHER INFORMATION: synthetic - CDRL2

<400> SEQUENCE: 11

Leu Val Ser Lys Leu Asp Ser
1               5

<210> SEQ ID NO 12
<211> LENGTH: 9
<212> TYPE: PRT
<213> ORGANISM: Artificial Sequence
<220> FEATURE:
<223> OTHER INFORMATION: synthetic - CDRL3

<400> SEQUENCE: 12

Trp Gln Gly Thr His Phe Pro Arg Thr
1               5

<210> SEQ ID NO 13
<211> LENGTH: 112
<212> TYPE: PRT
<213> ORGANISM: Artificial Sequence
<220> FEATURE:
<223> OTHER INFORMATION: synthetic - 10C2 heavy chain

<400> SEQUENCE: 13

Gln Val Gln Leu Glu Gln Ser Gly Pro Val Leu Val Lys Pro Gly Ala
1               5                   10                  15

Ser Val Lys Met Ser Cys Lys Ala Ser Gly Tyr Thr Phe Thr Asp Tyr
            20                  25                  30

Tyr Met Asn Trp Val Lys Gln Ser His Gly Lys Ser Leu Glu Trp Ile
        35                  40                  45

Gly Val Ile Asn Pro Tyr Asn Gly Gly Thr Ser Tyr Asn Gln Lys Phe
    50                  55                  60

Lys Gly Lys Ala Thr Leu Thr Val Asp Lys Ser Ser Thr Ala Cys
65                  70                  75                  80

Met Glu Leu Asn Cys Leu Thr Ser Glu Asp Ser Ala Val Tyr Cys
                85                  90                  95

Thr Leu Gly Ala Tyr Trp Gly Gln Gly Thr Ser Val Thr Val Ser Ser
            100                 105                 110

<210> SEQ ID NO 14
<211> LENGTH: 7
<212> TYPE: PRT
<213> ORGANISM: Artificial Sequence
<220> FEATURE:
<223> OTHER INFORMATION: synthetic - CDH1

<400> SEQUENCE: 14

Gly Tyr Thr Phe Thr Asp Tyr
1               5
```

```
<210> SEQ ID NO 15
<211> LENGTH: 5
<212> TYPE: PRT
<213> ORGANISM: Artificial Sequence
<220> FEATURE:
<223> OTHER INFORMATION: synthetic - CDH2

<400> SEQUENCE: 15

Asn Pro Tyr Asn Gly
1               5

<210> SEQ ID NO 16
<211> LENGTH: 3
<212> TYPE: PRT
<213> ORGANISM: Artificial Sequence
<220> FEATURE:
<223> OTHER INFORMATION: synthetic - CDH3

<400> SEQUENCE: 16

Gly Ala Tyr
1

<210> SEQ ID NO 17
<211> LENGTH: 107
<212> TYPE: PRT
<213> ORGANISM: Artificial Sequence
<220> FEATURE:
<223> OTHER INFORMATION: synthetic - 12B1 light chain

<400> SEQUENCE: 17

Asp Ile Val Met Thr Gln Thr Thr Ala Ser Leu Ser Thr Ser Val Gly
1               5                   10                  15

Glu Thr Val Thr Ile Thr Cys Arg Ala Ser Gly Asn Leu His Ser Tyr
            20                  25                  30

Leu Thr Trp Tyr Gln Gln Lys Gln Gly Lys Ser Pro Gln Leu Leu Val
        35                  40                  45

Tyr Asn Ala Lys Thr Leu Ala Asp Gly Val Pro Ser Arg Phe Ser Gly
    50                  55                  60

Ser Gly Ser Gly Thr Gln Tyr Ser Leu Lys Ile Asp Ser Leu Gln Pro
65                  70                  75                  80

Glu Asp Phe Gly Ser Tyr Tyr Cys Gln His Phe Trp Thr Thr Pro Phe
                85                  90                  95

Thr Phe Gly Ser Gly Thr Lys Leu Glu Ile Lys
            100                 105

<210> SEQ ID NO 18
<211> LENGTH: 11
<212> TYPE: PRT
<213> ORGANISM: Artificial Sequence
<220> FEATURE:
<223> OTHER INFORMATION: synthetic - CDRL1

<400> SEQUENCE: 18

Arg Ala Ser Gly Asn Leu His Ser Tyr Leu Thr
1               5                   10

<210> SEQ ID NO 19
<211> LENGTH: 7
<212> TYPE: PRT
<213> ORGANISM: Artificial Sequence
<220> FEATURE:
<223> OTHER INFORMATION: synthetic - CDRL2

<400> SEQUENCE: 19
```

Asn Ala Lys Thr Leu Ala Asp
1               5

<210> SEQ ID NO 20
<211> LENGTH: 9
<212> TYPE: PRT
<213> ORGANISM: Artificial Sequence
<220> FEATURE:
<223> OTHER INFORMATION: synthetic - CDRL3

<400> SEQUENCE: 20

Gln His Phe Trp Thr Thr Pro Phe Thr
1               5

<210> SEQ ID NO 21
<211> LENGTH: 120
<212> TYPE: PRT
<213> ORGANISM: Artificial Sequence
<220> FEATURE:
<223> OTHER INFORMATION: synthetic - 12B1 heavy chain

<400> SEQUENCE: 21

Glu Val Lys Leu Glu Glu Ser Gly Thr Glu Leu Val Lys Pro Gly Ala
1               5                   10                  15

Ser Val Lys Leu Ser Cys Lys Ala Ser Gly Tyr Thr Phe Thr Ser Tyr
            20                  25                  30

Trp Met His Trp Val Lys Gln Arg Pro Gly Gln Gly Leu Glu Trp Ile
        35                  40                  45

Gly Asn Ile Asn Pro Thr Asn Gly Gly Thr Asn Tyr Asn Glu Lys Phe
    50                  55                  60

Lys Ser Lys Ala Thr Leu Thr Val Asp Lys Ser Ser Arg Thr Ala Tyr
65                  70                  75                  80

Met Gln Leu Ser Ser Leu Thr Ser Gly Asp Ser Ala Val Tyr Tyr Cys
                85                  90                  95

Ala Arg Arg Asp Phe Ile Thr Thr Ser Gly Phe Ala Tyr Trp Gly Gln
            100                 105                 110

Gly Thr Leu Val Thr Val Ser Ala
        115                 120

<210> SEQ ID NO 22
<211> LENGTH: 7
<212> TYPE: PRT
<213> ORGANISM: Artificial Sequence
<220> FEATURE:
<223> OTHER INFORMATION: synthetic - CDH1

<400> SEQUENCE: 22

Gly Tyr Thr Phe Thr Ser Tyr
1               5

<210> SEQ ID NO 23
<211> LENGTH: 6
<212> TYPE: PRT
<213> ORGANISM: Artificial Sequence
<220> FEATURE:
<223> OTHER INFORMATION: synthetic - CDH2

<400> SEQUENCE: 23

Asn Pro Thr Asn Gly Gly
1               5

<210> SEQ ID NO 24
<211> LENGTH: 11

```
<212> TYPE: PRT
<213> ORGANISM: Artificial Sequence
<220> FEATURE:
<223> OTHER INFORMATION: synthetic - CDH3

<400> SEQUENCE: 24

Arg Asp Phe Ile Thr Thr Ser Gly Phe Ala Tyr
1               5                   10

<210> SEQ ID NO 25
<211> LENGTH: 107
<212> TYPE: PRT
<213> ORGANISM: Artificial Sequence
<220> FEATURE:
<223> OTHER INFORMATION: synthetic - 13H1 light chain

<400> SEQUENCE: 25

Asp Ile Val Met Thr Gln Thr Pro Lys Ser Met Ser Met Ser Val Gly
1               5                   10                  15

Glu Arg Val Thr Leu Ser Cys Lys Ala Ser Glu Asn Val Gly Thr Tyr
            20                  25                  30

Val Ser Trp Tyr Gln Gln Lys Pro Glu Gln Ser Pro Lys Val Leu Ile
        35                  40                  45

Tyr Gly Ala Ser Asn Arg Phe Thr Gly Val Pro Asp Arg Phe Thr Gly
    50                  55                  60

Ser Gly Ser Ala Thr Asp Phe Thr Leu Thr Ile Ser Ser Val Gln Thr
65                  70                  75                  80

Glu Asp Leu Ala Asp Tyr His Cys Gly Gln Ser Tyr Ser Tyr Pro Leu
                85                  90                  95

Thr Phe Gly Ala Gly Thr Lys Leu Glu Leu Lys
            100                 105

<210> SEQ ID NO 26
<211> LENGTH: 11
<212> TYPE: PRT
<213> ORGANISM: Artificial Sequence
<220> FEATURE:
<223> OTHER INFORMATION: synthetic - CDRL1

<400> SEQUENCE: 26

Lys Ala Ser Glu Asn Val Gly Thr Tyr Val Ser
1               5                   10

<210> SEQ ID NO 27
<211> LENGTH: 7
<212> TYPE: PRT
<213> ORGANISM: Artificial Sequence
<220> FEATURE:
<223> OTHER INFORMATION: synthetic - CDRL2

<400> SEQUENCE: 27

Gly Ala Ser Asn Arg Phe Thr
1               5

<210> SEQ ID NO 28
<211> LENGTH: 9
<212> TYPE: PRT
<213> ORGANISM: Artificial Sequence
<220> FEATURE:
<223> OTHER INFORMATION: synthetic - CDRL3

<400> SEQUENCE: 28

Gly Gln Ser Tyr Ser Tyr Pro Leu Thr
1               5
```

<210> SEQ ID NO 29
<211> LENGTH: 123
<212> TYPE: PRT
<213> ORGANISM: Artificial Sequence
<220> FEATURE:
<223> OTHER INFORMATION: synthetic - 13H1 heavy chain

<400> SEQUENCE: 29

```
Gln Val Gln Leu Gln Gln Ser Gly Thr Glu Leu Val Lys Pro Gly Ala
1               5                   10                  15

Ser Val Lys Leu Ser Cys Lys Ala Ser Gly His Thr Phe Thr Ser Tyr
            20                  25                  30

Trp Met His Trp Val Lys Gln Arg Pro Gly Gln Gly Leu Glu Trp Ile
        35                  40                  45

Gly Asn Ile Asn Pro Ser Asn Gly Gly Thr Asn Tyr Asn Glu Lys Phe
    50                  55                  60

Lys Ser Lys Ala Thr Leu Thr Val Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Arg Gly Tyr Tyr Gly Ser Ser Ser Tyr Trp Ser Phe Asp Val
            100                 105                 110

Trp Gly Thr Gly Thr Thr Val Thr Val Ser Ser
        115                 120
```

<210> SEQ ID NO 30
<211> LENGTH: 7
<212> TYPE: PRT
<213> ORGANISM: Artificial Sequence
<220> FEATURE:
<223> OTHER INFORMATION: synthetic - CDH1

<400> SEQUENCE: 30

```
Gly His Thr Phe Thr Ser Tyr
1               5
```

<210> SEQ ID NO 31
<211> LENGTH: 6
<212> TYPE: PRT
<213> ORGANISM: Artificial Sequence
<220> FEATURE:
<223> OTHER INFORMATION: synthetic - CDH2

<400> SEQUENCE: 31

```
Asn Pro Ser Asn Gly Gly
1               5
```

<210> SEQ ID NO 32
<211> LENGTH: 14
<212> TYPE: PRT
<213> ORGANISM: Artificial Sequence
<220> FEATURE:
<223> OTHER INFORMATION: synthetic - CDH3

<400> SEQUENCE: 32

```
Arg Gly Tyr Tyr Gly Ser Ser Ser Tyr Trp Ser Phe Asp Val
1               5                   10
```

<210> SEQ ID NO 33
<211> LENGTH: 107
<212> TYPE: PRT
<213> ORGANISM: Artificial Sequence
<220> FEATURE:
<223> OTHER INFORMATION: synthetic - 15B8 light chain

<400> SEQUENCE: 33

Asp Ile Val Met Thr Gln Thr Pro Ala Ser Leu Ser Ala Ser Val Gly
1               5                   10                  15

Glu Thr Val Thr Ile Thr Cys Arg Ala Ser Gly Asn Ile His Asn Tyr
            20                  25                  30

Leu Ala Trp Tyr Gln Gln Lys Gln Gly Lys Ser Pro Gln Leu Leu Val
        35                  40                  45

Tyr Asn Ala Lys Thr Leu Ala Asp Gly Val Pro Ser Arg Phe Ser Gly
    50                  55                  60

Ser Gly Ser Gly Thr Gln Tyr Ser Leu Lys Ile Asn Ser Leu Gln Pro
65                  70                  75                  80

Glu Asp Phe Gly Ser Tyr Tyr Cys Gln His Phe Trp Ser Thr Pro Phe
                85                  90                  95

Thr Phe Gly Ser Gly Thr Lys Leu Glu Ile Lys
            100                 105

<210> SEQ ID NO 34
<211> LENGTH: 11
<212> TYPE: PRT
<213> ORGANISM: Artificial Sequence
<220> FEATURE:
<223> OTHER INFORMATION: synthetic - CDRL1

<400> SEQUENCE: 34

Arg Ala Ser Gly Asn Ile His Asn Tyr Leu Ala
1               5                   10

<210> SEQ ID NO 35
<211> LENGTH: 7
<212> TYPE: PRT
<213> ORGANISM: Artificial Sequence
<220> FEATURE:
<223> OTHER INFORMATION: synthetic - CDRL2

<400> SEQUENCE: 35

Asn Ala Lys Thr Leu Ala Asp
1               5

<210> SEQ ID NO 36
<211> LENGTH: 9
<212> TYPE: PRT
<213> ORGANISM: Artificial Sequence
<220> FEATURE:
<223> OTHER INFORMATION: synthetic - CDRL3

<400> SEQUENCE: 36

Gln His Phe Trp Ser Thr Pro Phe Thr
1               5

<210> SEQ ID NO 37
<211> LENGTH: 121
<212> TYPE: PRT
<213> ORGANISM: Artificial Sequence
<220> FEATURE:
<223> OTHER INFORMATION: synthetic - 15B8 heavy chain

<400> SEQUENCE: 37

Gln Val Gln Leu Glu Gln Ser Gly Thr Glu Leu Val Lys Pro Gly Ala
1               5                   10                  15

Ser Val Lys Leu Ser Cys Lys Ala Ser Gly Tyr Thr Phe Thr Ser Tyr

```
                    20                  25                  30
Trp Met His Trp Val Lys Gln Arg Pro Gly Gln Gly Leu Glu Trp Ile
        35                  40                  45

Gly Asn Ile Asn Pro Ser Asn Gly Gly Thr Asn Tyr Asn Glu Lys Phe
        50                  55                  60

Lys Ser Lys Ala Thr Leu Thr Val Asp Lys Ser Ser Thr Ala Tyr
65                  70                  75                  80

Met Gln Leu Ser Ser Leu Thr Ser Glu Asp Ser Ala Ile Tyr Tyr Cys
                85                  90                  95

Ala Arg Arg Asn Asn Tyr Tyr Ala Ser Ser Pro Phe Ala Tyr Trp Gly
                100                 105                 110

Gln Gly Thr Leu Val Ser Val Ser Ala
            115                 120

<210> SEQ ID NO 38
<211> LENGTH: 7
<212> TYPE: PRT
<213> ORGANISM: Artificial Sequence
<220> FEATURE:
<223> OTHER INFORMATION: synthetic - CDH1

<400> SEQUENCE: 38

Gly Tyr Thr Phe Thr Ser Tyr
1               5

<210> SEQ ID NO 39
<211> LENGTH: 6
<212> TYPE: PRT
<213> ORGANISM: Artificial Sequence
<220> FEATURE:
<223> OTHER INFORMATION: synthetic - CDH2

<400> SEQUENCE: 39

Asn Pro Ser Asn Gly Gly
1               5

<210> SEQ ID NO 40
<211> LENGTH: 12
<212> TYPE: PRT
<213> ORGANISM: Artificial Sequence
<220> FEATURE:
<223> OTHER INFORMATION: synthetic - CDH3

<400> SEQUENCE: 40

Arg Asn Asn Tyr Tyr Ala Ser Ser Pro Phe Ala Tyr
1               5                   10
```